US009084612B2

(12) United States Patent
Sordelet et al.

(10) Patent No.: US 9,084,612 B2
(45) Date of Patent: Jul. 21, 2015

(54) FEMORAL ORTHOPAEDIC SURGICAL INSTRUMENTS AND METHOD OF USE OF SAME

(75) Inventors: Ben Sordelet, Warsaw, IN (US); Chad E. Derf, Warsaw, IN (US); Rebecca L. Chaney, Warsaw, IN (US); Craig S. Tsukayama, Fort Wayne, IN (US); Carl F. Livorsi, Lakeville, MA (US); Phillip G. Withee, Fall River, MA (US)

(73) Assignee: DEPUY (IRELAND) (IE)

( * ) Notice: Subject to any disclaimer, the term of this patent is extended or adjusted under 35 U.S.C. 154(b) by 331 days.

(21) Appl. No.: 13/485,502

(22) Filed: May 31, 2012

(65) Prior Publication Data

US 2013/0325016 A1 Dec. 5, 2013

Related U.S. Application Data

(60) Provisional application No. 61/653,359, filed on May 30, 2012.

(51) Int. Cl.
| | |
|---|---|
| A61B 17/56 | (2006.01) |
| A61B 17/15 | (2006.01) |
| A61B 17/16 | (2006.01) |
| A61B 17/17 | (2006.01) |
| A61B 17/02 | (2006.01) |
| A61B 19/00 | (2006.01) |

(52) U.S. Cl.
CPC ............ *A61B 17/155* (2013.01); *A61B 17/164* (2013.01); *A61B 17/1764* (2013.01); *A61B 2017/0268* (2013.01); *A61B 2019/461* (2013.01)

(58) Field of Classification Search
CPC .............................. A61B 17/56; A61B 17/155

USPC ........................................... 606/86 R, 87–89
See application file for complete search history.

(56) References Cited

U.S. PATENT DOCUMENTS

| | | | |
|---|---|---|---|
| 5,879,393 A * | 3/1999 | Whiteside et al. | 623/22.4 |
| 8,038,681 B2 | 10/2011 | Koenemann | |
| 2004/0039450 A1* | 2/2004 | Griner et al. | 623/20.31 |
| 2007/0073305 A1 | 3/2007 | Lionberger et al. | |
| 2009/0088762 A1* | 4/2009 | Koenemann | 606/88 |
| 2009/0125114 A1 | 5/2009 | May et al. | |
| 2013/0325014 A1 | 12/2013 | Sordelet et al. | |
| 2013/0325018 A1 | 12/2013 | Thomas et al. | |
| 2013/0325019 A1 | 12/2013 | Thomas et al. | |

(Continued)

FOREIGN PATENT DOCUMENTS

EP 0914806 5/1999

OTHER PUBLICATIONS

Zimmer NexGen LCCK, Surgical Technique for use with LCCK 4-in-1 Instrument, 2009, 52 pages.

(Continued)

*Primary Examiner* — Christopher Beccia
(74) *Attorney, Agent, or Firm* — Barnes & Thornburg LLP

(57) ABSTRACT

An orthopaedic surgical instrument assembly includes a base block, an intramedullary orthopaedic surgical instrument configured to be inserted into a medullary canal of a patient's femur, an adaptor, and a modular cutting block. The base cutting block includes a slot, and the adaptor is positioned in the slot. The adaptor includes a mounting bracket engaged with the base plate, and a fastener coupled to the intramedullary orthopaedic surgical instrument. The modular cutting block is configured to be secured to the base block.

20 Claims, 29 Drawing Sheets

(56) References Cited

U.S. PATENT DOCUMENTS

2013/0325021 A1    12/2013    Sordelet et al.
2013/0325136 A1    12/2013    Thomas et al.

OTHER PUBLICATIONS

DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.
GMK Revision, Surgical Technique, Ref. 99.27.12US rev. 1, Dec. 27, 1999, 74 pages.
European Search Report, European Application No. 13169556.1-1654, Sep. 3, 2013, 8 pages.
Declaration of Gary M. Lindsay dated Dec. 23, 2014, 5 pages.
Redacted Memorandum with Appendix A, dated Jan. 26, 2010, outlining a surgical instrument evaluation that commenced in 2010, 37 pages.
"ReInstall Wave 1 Evaluation Surgical Technique," used during the surgical instrument evaluation that commenced in 2010, 36 pages.
Tray configuration cards showing the instruments used during the surgical instrument evaluation that commenced in 2010, 8 pages.

* cited by examiner

FEMORAL ORTHOPAEDIC SURGICAL INSTRUMENTS AND METHOD OF USE OF SAME

This application claims priority under 35 U.S.C. §119 to U.S. Patent Application No. 61/653,359, which was filed on May 30, 2012 and is incorporated herein by reference.

CROSS-REFERENCE

Cross reference is made to copending U.S. patent application Ser. No. 13/485,497 entitled "METHOD OF ASSEMBLING AND POSITIONING A FEMORAL ORTHOPAEDIC SURGICAL INSTRUMENT"; and copending U.S. patent application Ser. No. 13/485,470 entitled "METHOD OF SURGICALLY PREPARING A PATIENT'S FEMUR, each of which is assigned to the same assignee as the present application, each of which is filed concurrently herewith, and each of which is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, reamers, drill guides, prosthetic trials, and other surgical instruments to prepare the patient's bones to receive the knee prosthesis.

SUMMARY

According to one aspect of the disclosure, an orthopaedic surgical instrument assembly is disclosed. The orthopaedic surgical instrument assembly includes a base cutting block, an intramedullary orthopaedic surgical instrument, and an adaptor. The base cutting block includes a base plate including a proximal surface, a distal surface positioned opposite the proximal surface, and a slot extending through the proximal surface and the distal surface. The base cutting block also includes a pair of curved arms extending posteriorly from the base plate. Each curved arm includes a posterior surface shaped to match a posterior condyle surface of a femoral prosthetic component and a cutting guide defined in the posterior surface. The intramedullary orthopaedic surgical instrument is configured to be inserted into a medullary canal of a patient's femur. The adaptor is positioned in the slot defined in the base plate. The adaptor includes a mounting bracket engaged with the base plate and a fastener coupled to the intramedullary orthopaedic surgical instrument.

In some embodiments, the base cutting block may include a locking tab pivotally coupled to the base plate. The locking tab may be moveable between a first position in which the locking tab is engaged with the mounting bracket to secure the adaptor to the base cutting block, and a second position in which the locking tab is disengaged from the mounting bracket such that the adaptor is removable from the base cutting block.

In some embodiments, the adaptor may further include an adaptor body coupled to the mounting bracket. The adaptor body may have a longitudinal axis that forms an oblique angle a distal surface of the mounting bracket.

In some embodiments, the locking tab of the base cutting block may be a first locking tab and the base cutting block may include a second locking tab pivotally coupled to the base plate. The mounting bracket may include a first arm extending outwardly from the adaptor body and a second arm extending outwardly from the adaptor body opposite the first arm. The first arm may have a channel defined therein that is sized to receive the first locking tab, and the second arm may have a channel defined therein that is sized to receive the second locking tab.

In some embodiments, the adaptor body may include a passageway that extends along the longitudinal axis, and the fastener may be pivotally coupled to the adaptor body. The fastener may include a threaded shaft extending outwardly from the adaptor body and a head retained in the passageway. The head may have a socket shaped to receive a surgical tool to rotate the fastener relative to the adaptor body.

Additionally, in some embodiments, the intramedullary orthopaedic surgical instrument may include a stem stabilizer having an internally-threaded first end. The internally-threaded first end may be engaged with the threaded shaft of the fastener. The stem stabilizer may also have an internally-threaded second end positioned opposite the first end. The intramedullary orthopaedic surgical instrument may be a stem trial including an externally-threaded end that is engaged with the internally-threaded second end of the stem stabilizer.

In some embodiments, the stem stabilizer may include a body having the first end and the second end and a pair of fins extending outwardly from the body.

In some embodiments, the orthopaedic surgical instrument assembly may further include a guide block configured to be positioned in the slot defined in the base plate in place of the adaptor. The guide block may include a mounting bracket configured to engage with the base cutting block, and a bushing having a cylindrical passageway defined therein sized to receive an orthopaedic surgical instrument.

In some embodiments, the orthopaedic surgical instrument assembly may further include a plurality of modular cutting blocks configured to be separately secured to an anterior side of the base plate.

According to another aspect of the disclosure, an orthopaedic surgical instrument assembly includes a base cutting block. The base cutting block has a base plate including a proximal surface, a distal surface positioned opposite the proximal surface, and a slot extending through the proximal surface and the distal surface. The base cutting block also includes a locking tab having a body positioned between the proximal surface and the distal surface of the base plate and an ear. The body of the locking tab is pivotally coupled to the base plate and moveable between a first position in which the ear of the locking tab is positioned in the slot and a second position in which the ear is spaced apart from the slot. The base cutting block has a pair of curved arms extending posteriorly from the base plate. Each curved arm includes a posterior surface shaped to match a posterior condyle surface of a femoral prosthetic component and a cutting guide defined in the posterior surface.

In some embodiments, the orthopaedic surgical instrument assembly may further include a first orthopaedic surgical instrument including a mounting bracket. When the body of the locking tab is in the first position, the ear of the locking tab may be engaged with the mounting bracket to secure the first orthopaedic surgical instrument to the base plate. When the body is in the second position, the ear of the locking tab may be disengaged from the mounting bracket such that the first orthopaedic surgical instrument is removable from the base plate.

Additionally, in some embodiments, the orthopaedic surgical instrument assembly may further include a second orthopaedic surgical instrument configured to be secured to a proximal end of the first orthopaedic surgical instrument. The second orthopaedic surgical instrument may be an intramedullary orthopaedic surgical instrument.

In some embodiments, the orthopaedic surgical instrument assembly may further include a plurality of modular cutting blocks configured to be separately secured to an anterior side of the base plate. In some embodiments, the plurality of modular cutting blocks may include an anterior cutting block having an anterior cutting guide.

Additionally, in some embodiments, at least one of the cutting guides defined in the curved arms of the base cutting block may define an imaginary plane. In some embodiments, the plurality of modular cutting blocks may include a distal cutting block configured to be secured to the base plate in place of the anterior cutting block. The distal cutting block may have a plurality of distal cutting guides. When the distal cutting block is secured to the base plate, each distal cutting guide may extend transverse to the imaginary plane and parallel to the other distal cutting guides.

In some embodiments, the plurality of modular cutting blocks may include a notch cutting block configured to be secured to the base plate in place of the anterior cutting block. The notch cutting block may include a first cutting guide having a first cutting guide surface that extends transverse to the imaginary plane, and a second cutting guide surface connected to the first cutting guide surface. The second cutting guide surface may extend transverse to the imaginary plane and orthogonal to the first cutting guide surface.

In some embodiments, the notch cutting block may further include a second cutting guide that extends obliquely relative to the imaginary plane.

In some embodiments, the orthopaedic surgical instrument assembly may further include a spacer block configured to be secured to the proximal surface of the base cutting block. In some embodiments, the orthopaedic surgical instrument assembly may further include a shim sized to be received in one of the cutting guides defined in the curved arms of the base cutting block.

According to another aspect, an orthopaedic surgical instrument assembly includes a base block, an intramedullary orthopaedic surgical instrument configured to be inserted into a medullary canal of a patient's femur, an adaptor, and a plurality of modular cutting blocks. The base block includes a base plate including a proximal surface, a distal surface positioned opposite the proximal surface, and a slot extending through the proximal surface and the distal surface. The intramedullary orthopaedic surgical instrument is configured to be inserted into a medullary canal of a patient's femur. The adaptor is positioned in the slot defined in the base plate. The adaptor includes a mounting bracket engaged with the base plate, and a fastener coupled to the intramedullary orthopaedic surgical instrument. The plurality of modular cutting blocks is configured to be separately secured to an anterior side of the base plate.

According to another aspect, a method of surgically preparing a distal end of a femur for implantation of a femoral prosthetic component is disclosed. The method includes positioning a base cutting block and an intramedullary adaptor on the distal end of the femur such that a first end of the intramedullary adaptor is received in the medullary canal of the femur and the intramedullary adaptor is secured to the base cutting block, attaching a first modular cutting block to an anterior side of the base cutting block, and resecting a first portion of the distal end of the femur using a cutting guide defined in the first modular cutting block. The method also includes resecting a first portion of the distal end of the femur using a base cutting guide defined in the base cutting block, attaching a second modular cutting block to the anterior side of the base cutting block in place of the first modular cutting block, and resecting a third portion of the distal end of the femur using a cutting guide defined in the second modular cutting block. The cutting guide of the second modular cutting block extends transverse to the imaginary plane defined by the base cutting guide.

In some embodiments, the method may further include determining an amount of bone to be resected when the second modular cutting block is attached to the base cutting block, and selecting from a plurality of cutting guides defined in a body plate of the second modular cutting block the cutting guide corresponding to the amount of bone to be resected. In some embodiments, the method of claim may further include pivoting a pin guide of the second modular cutting block relative to the body plate while maintaining the body plate in position on an anterior surface of the femur, and inserting a pin through a passageway defined in the pin guide into the anterior surface of the femur.

In some embodiments, the method may further include attaching a third modular cutting block to the anterior side of the base cutting block prior to attaching the first modular cutting block to the anterior side of the base cutting block, and resecting a fourth portion of the distal end of the femur using a cutting guide defined in the third modular cutting block that extends transverse to the imaginary plane defined by the base cutting guide.

In some embodiments, resecting the third portion of the distal end of the femur may include advancing a cutting saw blade into contact with the distal end of the femur along a first cutting guide surface extending transverse to the imaginary plane defined by the base cutting guide, and advancing the cutting saw blade into contact with the distal end of the femur along a second cutting guide surface extending transverse to the imaginary plane and orthogonal to the first cutting guide surface.

Additionally, in some embodiments, the method may include resecting a fourth portion of the distal end of the femur using a chamfer cutting guide defined in the second modular cutting block. The chamfer cutting guide may extend obliquely relative to the imaginary plane defined by the base cutting guide.

In some embodiments, the method may include selecting the base cutting guide from a plurality of base cutting guides defined in the base cutting block. In some embodiments, positioning the base cutting block and the intramedullary adaptor on the distal end of the femur may include rotating the base cutting block and the intramedullary adaptor on the distal end of the femur relative to an intramedullary orthopaedic surgical instrument positioned in the medullary canal of the femur, and fixing the base cutting block and the intramedullary adaptor relative to the intramedullary surgical instrument.

In some embodiments, the intramedullary orthopaedic surgical instrument may include a stem trial positioned in the medullary canal of the femur.

In some embodiments, the method may further include detaching the intramedullary adaptor from the base cutting block, attaching a guide block to the base cutting block in place of the intramedullary adaptor, and reaming the distal end of the femur using a passageway defined in the guide block.

According to another aspect, a method of surgically preparing a distal end of a femur for implantation of a femoral prosthetic component includes positioning a base cutting block and an intramedullary adaptor on the distal end of the femur such that a first end of the intramedullary adaptor is received in the medullary canal of the femur and the intramedullary adaptor is secured to the base cutting block, resecting the femur using a posterior cutting guide defined in the base cutting block, attaching an anterior cutting block to an anterior side of the base cutting block, resecting the femur using an anterior cutting guide defined in the anterior cutting block, attaching a notch cutting block to the anterior side of the base cutting block in place of the anterior cutting block, and resecting the femur using a notch cutting guide defined in the notch cutting block to form a notch in the femur sized to receive a femoral box of the femoral prosthetic component.

In some embodiments, the method may further include resecting the femur using a chamfer cutting guide defined in the notch cutting block. Additionally, in some embodiments, the method may further include resecting the femur using a second chamfer cutting guide defined in the base cutting block.

In some embodiments, the method may also include detaching the intramedullary adaptor from the base cutting block, attaching a guide block to the base cutting block in place of the intramedullary adaptor, and reaming the distal end of the femur using a passageway defined in the guide block.

In some embodiments, the method may further include detaching a cover from the base cutting block to expose a pair of mounting shafts formed on the anterior side of the base cutting block. In some embodiments, attaching the anterior cutting block to the anterior side of the base cutting block may include positioning the anterior cutting block over the pair of mounting shafts.

In some embodiments, the method may include attaching a distal cutting block to the anterior side of the base cutting block, and resecting the femur using a distal cutting guide defined in the distal cutting block.

Additionally, in some embodiments, the method may include selecting the distal cutting guide from a plurality of distal cutting guides defined in the distal cutting block.

According to another aspect, a method of surgically preparing a distal end of a femur for implantation of a femoral prosthetic component includes attaching a first end of an intramedullary adaptor to an intramedullary orthopaedic surgical instrument positioned in the medullary canal of the femur, rotating the intramedullary adaptor and a base cutting block on the distal end of the femur relative to the intramedullary surgical instrument, fixing the base cutting block and the intramedullary adaptor relative to the intramedullary surgical instrument, attaching a first modular cutting block to an anterior side of the base cutting block, resecting the femur using an anterior cutting guide defined in the first modular cutting block, attaching a second modular cutting block to the anterior side of the base cutting block in place of the first modular cutting block, and resecting the femur using an anterior chamfer cutting guide defined in the second modular cutting block.

In some embodiments, the method may further include attaching a third modular cutting block to the anterior side of the base cutting block prior to attaching the first modular cutting block to the base cutting block, selecting a distal cutting guide from a plurality of distal cutting guides defined in the third modular cutting block, and resecting the femur using the distal cutting guide selected from the plurality of distal cutting guides.

According to another aspect, a method for performing an orthopaedic surgical procedure on a femur includes positioning a distal end of an intramedullary adaptor in a slot defined in a base cutting block, securing the distal end of the intramedullary adaptor to the base cutting block, attaching a proximal end of the intramedullary adaptor to an intramedullary orthopaedic surgical instrument after securing the intramedullary adaptor to the base cutting block, and positioning the base cutting block on a distal end of the femur.

In some embodiments, the method may include advancing the intramedullary orthopaedic surgical instrument through an opening defined in the distal end of the femur into the medullary canal after attaching the intramedullary adaptor to the intramedullary surgical instrument. In some embodiments, the method may further include securing a stem trial to a stem stabilizer to form the intramedullary orthopaedic surgical instrument.

Additionally, in some embodiments, the stem stabilizer may have a plurality of fins extending outwardly therefrom, and advancing the intramedullary orthopaedic surgical instrument into the medullary canal may include engaging the plurality of fins with bone surrounding the medullary canal.

In some embodiments, attaching the proximal end of the intramedullary adaptor to the intramedullary orthopaedic surgical instrument may include threading a shaft of the intramedullary adaptor into an internally-threaded distal end of the intramedullary surgical instrument. In some embodiments, securing the distal end of the intramedullary adaptor to the base cutting block may include advancing a locking tab of the base cutting block into a channel defined in the intramedullary adaptor.

In some embodiments, the method may further include attaching a modular cutting block to an anterior surface of the base cutting block, and resecting the femur using a cutting guide defined in the modular cutting block.

In some embodiments, the method may further include assessing a gap defined between the base cutting block attached to the femur and a tibial component attached to a corresponding tibia. In some embodiments, assessing the gap may include selecting a shim from a plurality of shims, attaching the shim to an end of a handle, and advancing the shim and the end of the handle into contact with the base cutting block and the tibial component.

Additionally, in some embodiments, the method may include permitting relative axial rotation between the proximal end of the intramedullary adaptor and the intramedullary orthopaedic surgical instrument. In some embodiments, the relative axial rotation is limited by a lug extending from the intramedullary adaptor.

According to another aspect, the method includes securing a stem trial to a stem stabilizer to form an intramedullary orthopaedic surgical instrument, securing a proximal end of an intramedullary adaptor to a distal end of the stem stabilizer, positioning a mounting bracket of the intramedullary adaptor in a slot defined in a base cutting block, placing a locking tab of the base cutting block in a channel defined in the mounting bracket of the intramedullary adaptor, advancing the intramedullary orthopaedic surgical instrument and the proximal end of the intramedullary adaptor through an opening defined in a distal end of the femur, and positioning the base cutting block on the distal end of the femur.

In some embodiments, securing the proximal end of an intramedullary adaptor to the distal end of the stem stabilizer may include aligning a shaft of the intramedullary adaptor with an aperture defined in the distal end of the stem stabilizer, and rotating the shaft of the intramedullary adaptor in a first direction to advance the shaft into the aperture and prevent an adaptor body of the intramedullary adaptor from moving relative to the stem stabilizer.

In some embodiments, the method may include rotating the shaft of the intramedullary adaptor in a second direction opposite the first direction to permit the adaptor body to rotate relative to the stem stabilizer, and rotating the intramedullary adaptor and the base cutting block relative to the stem stabilizer.

In some embodiments, the method may further include selecting a shim having a predetermined thickness from a plurality of shims, attaching the shim to a handle, and inserting the shim and the handle between the base cutting block and a tibial component secured to a proximal end of a tibia. Rotating the intramedullary adaptor and the base cutting block may be performed after the shim and the handle are inserted.

In some embodiments, the method may further include assessing a gap defined between the base cutting block and a tibial component.

According to another aspect, the method may include attaching a proximal end of an intramedullary adaptor to an intramedullary orthopaedic surgical instrument, securing a distal end of an intramedullary adaptor to a base cutting block, inserting the intramedullary orthopaedic surgical instrument into a medullary canal using the base cutting block, and positioning the base cutting block on a distal end of the femur. In some embodiments, the method may further include attaching a modular cutting block to an anterior surface of the base cutting block, and resecting the femur using a cutting guide defined in the modular cutting block.

BRIEF DESCRIPTION OF THE DRAWINGS

The detailed description particularly refers to the following figures, in which.

DETAILED DESCRIPTION OF THE DRAWINGS

Figure 1:
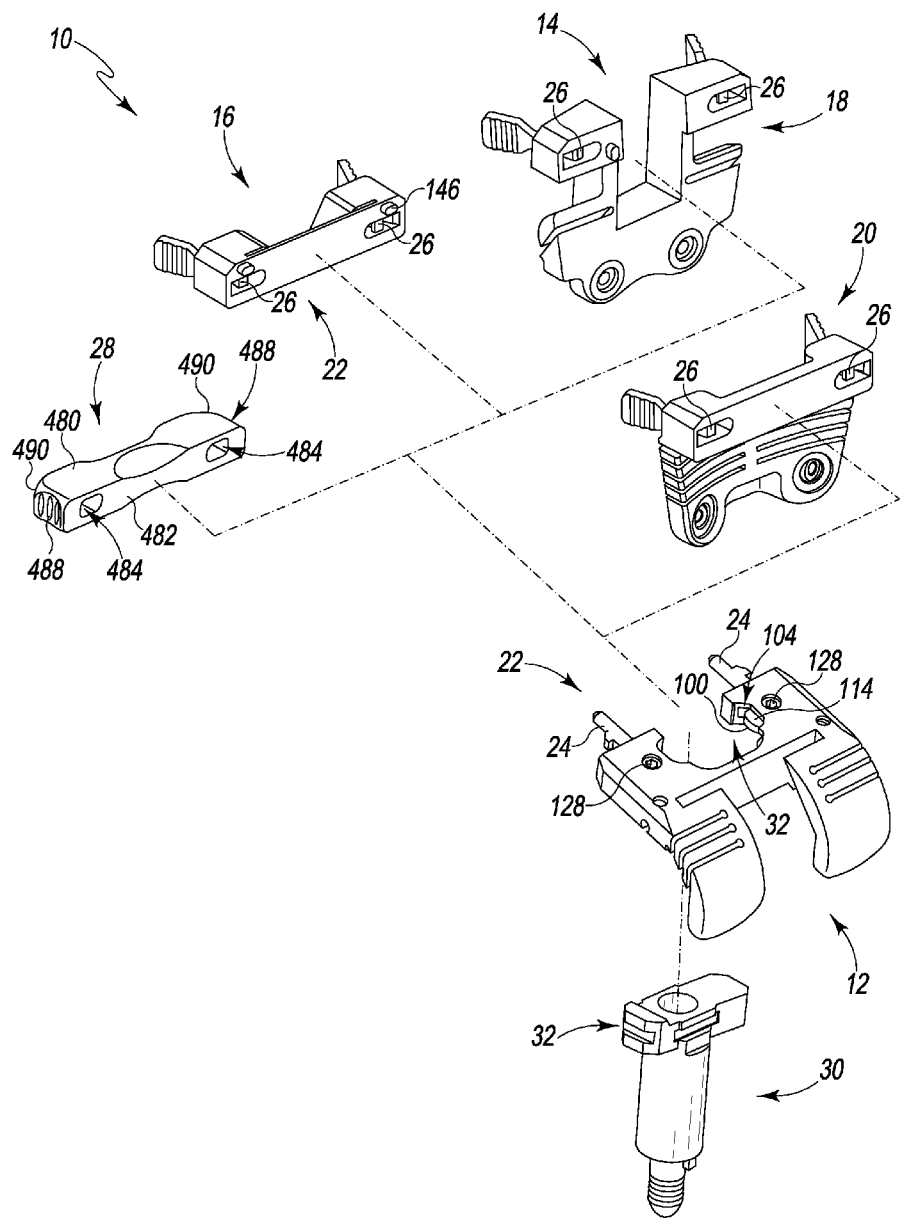
FIG. 1 is an exploded view of an exemplary embodiment of an orthopaedic surgical instrument assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument assembly 10 (hereinafter instrument assembly 10) is shown. What is meant herein by the term "orthopaedic surgical instrument" or "orthopaedic surgical instrument assembly" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient. The instrument assembly 10 includes a base cutting block 12 configured for use on a femur of a patient, as described in greater detail below.

The instrument assembly 10 also includes a plurality of modular cutting blocks 14 configured to be coupled to the base cutting block 12. In the illustrative embodiment, the modular cutting blocks 14 include an anterior cutting block 16, a notch cutting block 18, and a distal cutting block 20. As described in greater detail below, each modular cutting block 14 may be secured to the base cutting block 12 in place of the other modular cutting blocks 14 during the orthopaedic surgical procedure. For example, the anterior cutting block 16 may be secured to the base cutting block 12 at one point during the orthopaedic surgical procedure, and the notch cutting block 18 or the distal cutting block 20 may be secured to the base cutting block 12 in place of the anterior cutting block 16 at other points during the orthopaedic surgical procedure.

The instrument assembly 10 includes a locking or retention mechanism 22 that secures each modular cutting block 14 to the base cutting block 12. In the illustrative embodiment, the retention mechanism 22 includes a pair of mounting brackets 24 attached to the base cutting block 12 and a pair of mounting brackets 26 attached to the modular cutting block 14. As described in greater detail below, the mounting brackets 26 of a modular cutting block 14 are configured to engage the mounting brackets 24 of the base cutting block 12 when the modular cutting block 14 is secured to the base cutting block 12, thereby securing the blocks together. The instrument assembly 10 also includes a cover 28, which may be positioned over the mounting brackets 24 of the base cutting block 12 when none of the modular cutting blocks 14 are secured to the base cutting block 12.

As shown in FIG. 1, the instrument assembly 10 also includes an intramedullary adaptor 30 configured to be coupled to the base cutting block 12. What is meant herein by the term "intramedullary adaptor" is a surgical tool configured to be secured to an intramedullary orthopaedic surgical instrument and including an end sized and shaped to be positioned in a medullary canal of a patient's femur during the orthopaedic surgical procedure. What is meant herein by the term "intramedullary orthopaedic surgical instrument" is a surgical tool configured to be positioned in the medullary canal of the patient's femur during the orthopaedic surgical procedure. Examples of intramedullary orthopaedic surgical instruments include femoral stem trials, femoral broaches, and the like. The instrument assembly 10 includes a locking mechanism 32 that secures the intramedullary adaptor 30 to the base cutting block 12, as described in greater detail below.

Figure 2:
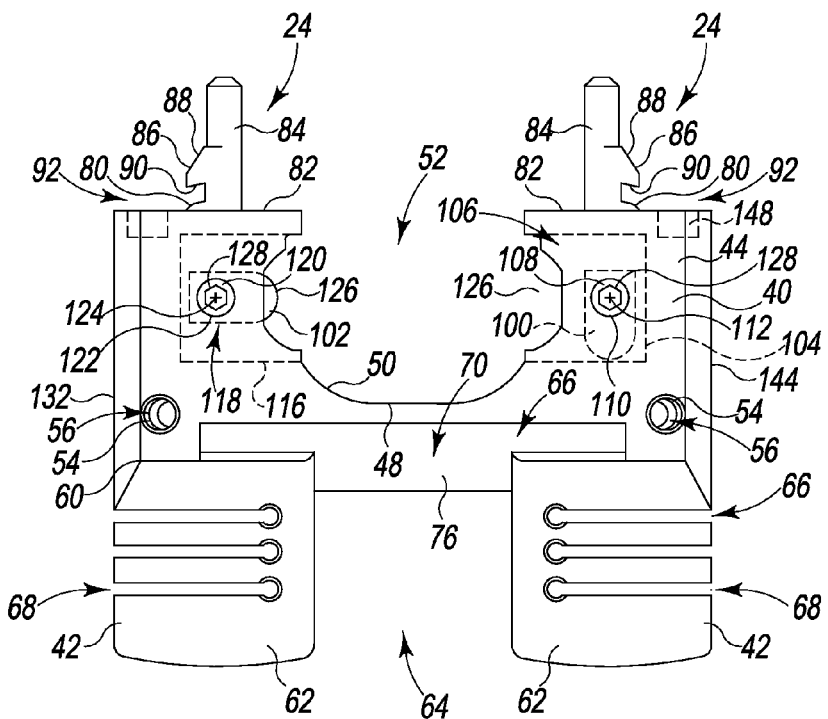
FIG. 2 is a perspective view of a base cutting block of the instrument assembly of FIG. 1.
Figure 3:
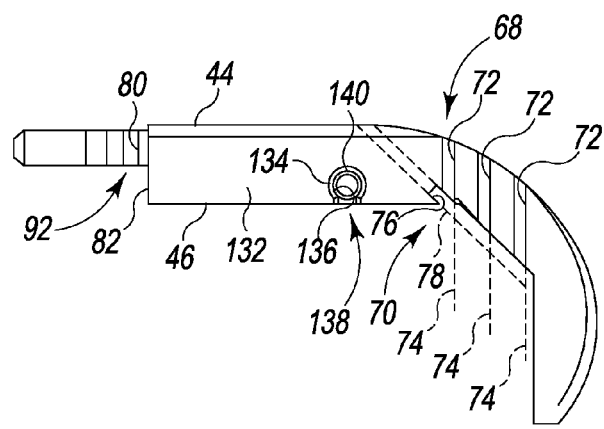
FIG. 3 is a side elevation view of the base cutting block of FIG. 2.

Referring now to FIGS. 2 and 3, the base cutting block 12 includes a base plate 40 and a pair of arms 42 extending from the base plate 40. The base plate 40 and the arms 42 of the base cutting block 12 are formed from a metallic material, such as, for example, a stainless steel or a cobalt chromium alloy. The base plate 40 includes a distal surface 44 and a proximal surface 46 positioned opposite the distal surface 44. An opening 48 is defined in the distal surface 44, and an inner wall 50 extends distally through the base plate 40 to define a receiving slot 52. As described in greater detail below, the slot 52 is sized to permit the passage of the intramedullary adaptor 30 and various other surgical tools.

The base cutting block 12 also includes a pair of fastener guides 54 that are defined in the base plate 40. Each fastener guide 54 includes a bore 56 that is sized to receive fasteners such as, for example, fixation pins 58 (see FIG. 24), which may be utilized to secure the base cutting block 12 to the patient's femur. It should be appreciated that in other embodiments the base cutting block 12 may include additional fastener guides 54 or other fastening elements to secure the cutting block to the patient's femur.

The arms 42 of the base cutting block 12 extends posteriorly from a posterior side 60 of the base cutting block 12. Each arm 42 includes an articulating surface 62 shaped to match a condylar surface of a femoral prosthetic component. In that way, the articulating surfaces 62 of the arms 42 are configured to contact a natural or prosthetic bearing surface of the patient's tibia. The arms 42 are spaced apart such that an opening 64 is defined therebetween.

The base cutting block 12 includes a number of cutting guides 66 that may be used during an orthopaedic surgical procedure to resect a portion of a patient's femur. For example, as shown in FIG. 2, the base cutting block 12 includes a number of posterior cutting guides 68 defined in the arms 42 and a posterior chamfer cutting guide 70 defined in the base plate 40. Each cutting guide 66 includes an elongated slot sized to receive a cutting saw blade of a surgical saw or other surgical device.

In the illustrative embodiment, each arm 42 has three posterior cutting guides 68 defined in the articulating surface 62 thereof. Each posterior cutting guide 68 includes a planar surface 72 that extends inwardly from the articulating surface 62. Each planar surface 72 defines a resection plane 74 that extends through a portion of the posterior condyles of the patient's femur when the base cutting block 12 is positioned thereon. In that way, the cutting guides 68 may be used by the orthopaedic surgeon during the resection of the patient's femur. As shown in FIG. 3, the resection planes 74 of the cutting guides 68 extend parallel to, and are spaced from, each other. In the illustrative embodiment, the cutting guides 68 are spaced apart from each other by about four millimeters. It should be appreciated that in other embodiments the arms 42 may include additional or fewer cutting guides 66 to provide the surgeon with other resection planes.

As shown in FIG. 2, the posterior chamfer cutting guide 70 defined in the base plate 40 includes a planar surface 76 that extends inwardly from the distal surface 44. The planar surface 76 defines a resection plane 78 that extends through a portion of the posterior condyles of the patient's femur when the base cutting block 12 is positioned thereon. In that way, the cutting guides 68 may be used by the orthopaedic surgeon during the resection of the patient's femur. As shown in FIG. 3, the resection plane 78 of the posterior chamfer cutting guide 70 extends obliquely relative to the resection planes 74 defined by the posterior cutting guides 68 such that an obtuse angle is defined between the planes 74, 78. In other embodiments, the base cutting block 12 may also include an anterior chamfer cutting guide positioned opposite the posterior chamfer cutting guide 70.

As described above, the instrument assembly 10 includes a retention mechanism 22, and the base cutting block 12 has a pair of mounting brackets 24 of that retention mechanism 22. As shown in FIGS. 2 and 3, each mounting bracket 24 includes a hub 80 attached to the anterior side surface 82 of the base cutting block 12 and a shaft 84 that extends anteriorly from the hub 80. A flange 86 extends outwardly from each shaft 84, and each flange 86 includes an anterior cam surface 88 and a posterior surface 90. A recess 92 is defined between is defined between the posterior surface 90 of each flange 86 and each hub 80. As described in greater detail below, the recesses 92 of the mounting brackets 24 are sized to receive catches 94 of the mounting brackets 26 of a modular cutting block 14 to secure the block 14 to the base cutting block 12.

As described above, the instrument assembly 10 includes a locking mechanism 32 to secure the intramedullary adaptor 30 to the base cutting block 12. In the illustrative embodiment, the locking mechanism 32 includes a pair of locking tabs 100, 102 pivotally coupled to the base cutting block 12. As shown in FIG. 1, the inner wall 50 of the base cutting block 12 has an aperture 104 defined therein, and the locking tab 100 is positioned in the aperture 104. The locking tab 100 is coupled to the base cutting block 12 via a joint 106. The joint 106 includes a pin 108 that extends from the locking tab 100 and is received in a bore 110 defined in the distal surface 44 of the base plate 40. The locking tab 100 is configured to pivot about an axis 112 defined by the pin 108 between a locked position (see FIG. 1) and an unlocked position (see FIG. 2). In the locked position, an ear 114 of the locking tab 100 is positioned in the receiving slot 52 of the base cutting block 12 to thereby engage a surgical instrument (e.g., the intramedullary adaptor 30) positioned in the slot 52. In the unlocked position, the ear 114 is positioned in the aperture 104 and spaced apart from the receiving slot 52.

The inner wall 50 of the base cutting block 12 has another aperture 116 defined therein opposite the aperture 104. The locking tab 102 is positioned in the aperture 116 and is coupled to the base cutting block 12 via a joint 118. The joint 118 includes a pin 120 that extends from the locking tab 102 and is received in a bore 122 defined in the distal surface 44 of the base plate 40. The locking tab 102 is configured to pivot about an axis 124 defined by the pin 120 between a locked position (see FIG. 2) and an unlocked position (see FIG. 1). In the locked position, an ear 126 of the locking tab 102 is positioned in the receiving slot 52 of the base cutting block 12 to thereby engage a surgical instrument (e.g., the intramedullary adaptor 30) positioned in the slot 52. In the unlocked position, the ear 126 is positioned in the aperture 116 and spaced apart from the receiving slot 52.

As shown in FIG. 2, each pin 108, 120 of the locking mechanism 32 has a socket 128 defined in an outer surface thereof. The sockets 128 are accessible through the bores 110, 122 of the base plate 40, and each socket 128 is sized and shaped to receive a corresponding end of a surgical tool. In an orthopaedic surgical procedure, a surgeon may insert the surgical tool into the socket 128 to move the respective locking tab 100, 102 between the locked position and the unlocked position. It should be appreciated that in other embodiments the locking mechanism may include threaded fasteners, latches, pins, or other structures necessary to secure the base cutting block 12 to another surgical instrument.

As shown in FIG. 3, the base plate 40 of the base cutting block 12 has a side wall 132 that extends between the distal surface 44 and the proximal surface 46. The side wall 132 has an opening 134 defined therein, and an inner wall 136 extends inwardly from the opening 134 to define a channel 138 in the proximal surface 46. The channel 138 includes a cylindrical segment 140 that is sized to receive a corresponding cylindrical pin 142, as described in greater detail below. The channel 138 is aligned with one of the fastener guides 54 such that the bore 56 of the fastener guide 54 opens into the cylindrical segment 140. The base plate 40 has another side wall 144 that is positioned opposite the side wall 132. Another channel (not shown) that is the mirror of the channel 138 extends inwardly from an opening defined in the side wall 144.

Figure 4:
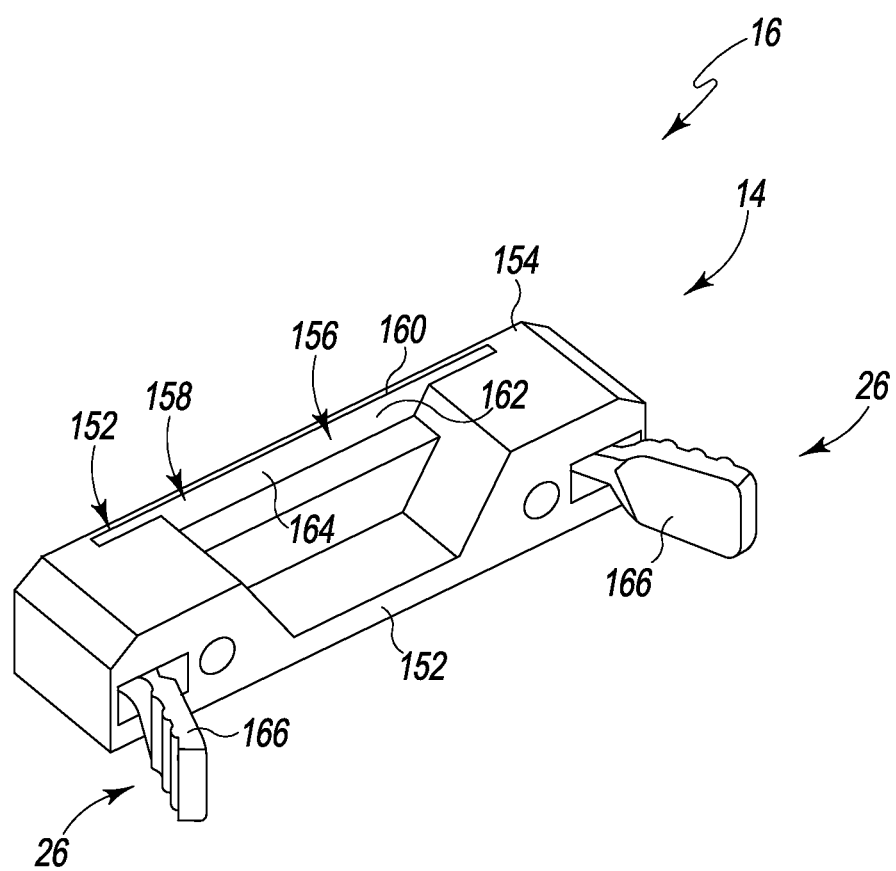
FIG. 4 is a perspective view of an anterior cutting block of the instrument assembly of FIG. 1.
Figure 5:
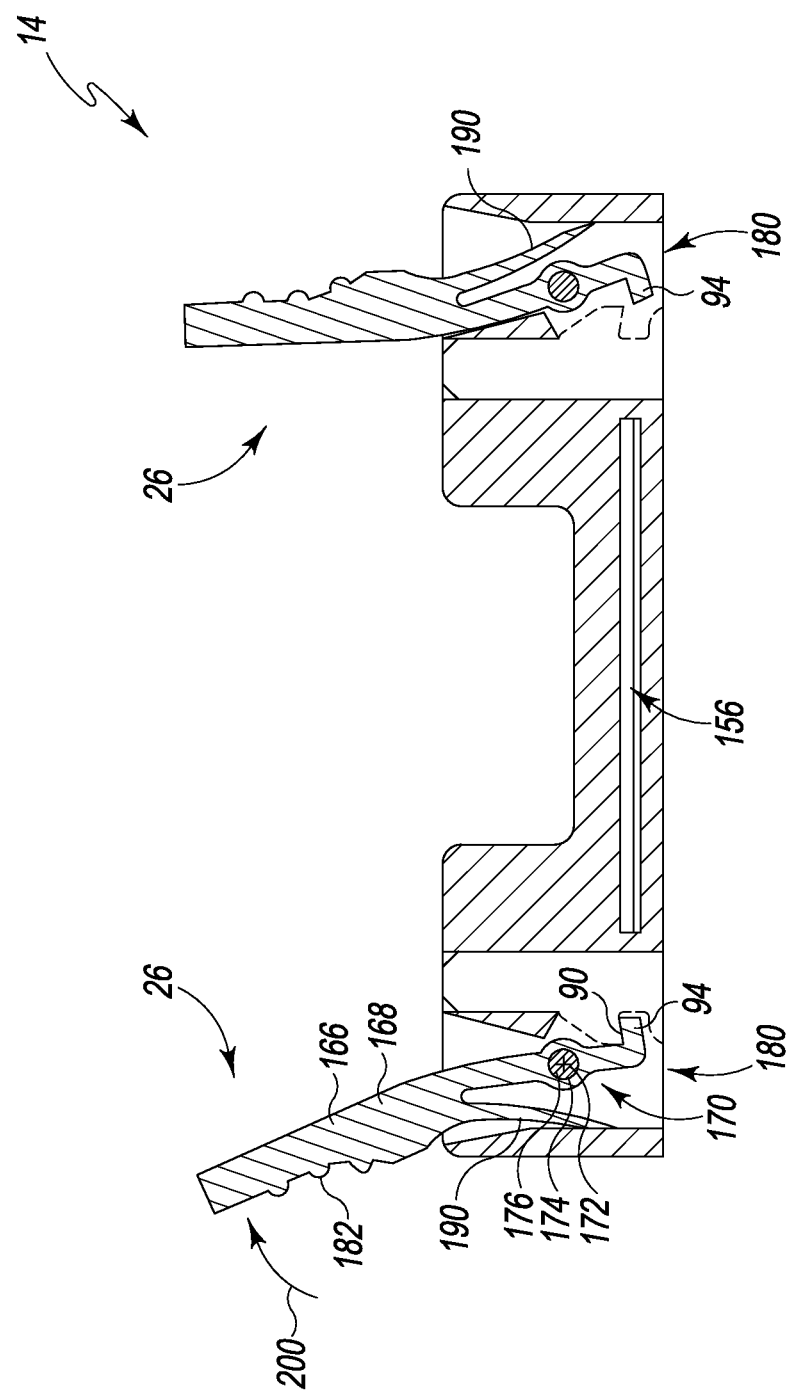
FIG. 5 is a cross-sectional side elevation view of the anterior cutting block of FIG. 4.

As described above, the instrument assembly 10 includes a number of modular cutting blocks 14 configured to be secured to the base cutting block 12. Each of the modular cutting blocks 14 is formed from a metallic material, such as, for example, a stainless steel or a cobalt chromium alloy. Referring now to FIGS. 4 and 5, the modular cutting blocks 14 include an anterior cutting block 16. The anterior cutting block 16 includes a posterior side wall 150 that confronts the anterior side surface 82 of the base cutting block 12 when the anterior cutting block 16 is secured to the block 12. An alignment pin 146 extends outwardly from the posterior side wall 150, and that pin 146 is received in an aperture 148 defined in the base cutting block 12 (see FIG. 2). The anterior cutting block 16 also includes an anterior side wall 152 that is positioned opposite the posterior side wall 150. A distal surface 154 extends between the side walls 150, 152.

The anterior cutting block 16 includes an anterior cutting guide 156 that may be used during an orthopaedic surgical procedure to resect an anterior portion of the patient's femur. The anterior cutting guide 156 includes an elongated slot 158 that extends inwardly from an opening 160 defined in the distal surface 154. The elongated slot 158 is sized to receive a cutting saw blade of a surgical saw or other surgical device. The cutting guide 156 includes a planar surface 162 that is connected to the distal surface 154, and the planar surface 162 defines a resection plane 164 that extends through an anterior portion of the patient's femur when the anterior cutting block 16 is secured to the base cutting block 12 on the patient's femur.

As described above, the instrument assembly 10 includes a retention mechanism 22 configured to secure each modular cutting block 14 to the base cutting block 12. Each modular cutting block 14 has a pair of mounting brackets 26 configured to engage the mounting brackets 24 of the base cutting block 12, thereby securing the modular cutting block 14 to the block 12. As shown in FIG. 5, each mounting bracket 26 includes a lever arm 166 pivotally coupled to the modular cutting block 14 (in this case, the anterior cutting block 16). The lever arm 166 includes a lever body 168 pivotally coupled to the modular cutting block 14 via a joint 170. The joint 170 includes a cylindrical pin 172 that extends through a mounting hole 174 defined in the lever body 168. Each end (not shown) of the pin 172 is received in an aperture defined in the modular cutting block. The pin 172 defines an axis 176 about which the lever arm 166 may pivot.

As shown in FIG. 5, the lever body 168 of the arm 166 is positioned in a passageway 180 extending through the modular cutting block 14. A handle 182 is formed on one end of the lever body 168 and extends outwardly from the passageway 180. A catch 94 is formed on the opposite end of the lever body 168. As described above, the catch 94 is received in one of the recesses 92 defined in the mounting brackets 24 of the base cutting block 12. The catch 94 includes an engagement surface 184 that engages a posterior surface 90 of the mounting brackets 24 to secure the modular cutting block 14 to the base cutting block 12.

As described above, the lever arm 166 is configured to pivot about the axis 176, and is moveable between an engaged position (see left side of FIG. 5) and a disengaged position (see right side of FIG. 5). The mounting bracket 26 also includes a biasing element 190 that biases the lever arm 166 is the engaged position. As shown in FIG. 5, the biasing element 190 is a cantilever spring having an end 192 attached to the lever arm 166 and another end 194 engaged with an inner wall 196 of the mounting bracket 26. It should be appreciated that in other embodiments the biasing element 190 may be, for example, a coil, torsion, or other spring.

In use, a surgeon or other user grasps the handles 182 of the lever arms 166 and pushes in the direction indicated by arrow 200. When the bias exerted by the springs 190 is overcome, the lever arm 166 is pivoted about the axis 176 from the engaged position to the disengaged position. The shafts 84 of the base cutting block 12 may then be aligned with the passageways 180 defined in the modular cutting block 14. The modular cutting block 14 may then be advanced over the shafts 84 such that the modular cutting block 14 confronts the anterior side surface 82 of the base cutting block 12. The surgeon may then release the handles 182, thereby permitting the lever arms 166 to pivot back to the engaged position. In the engaged position, the catch 94 is received in the recess 92 of the mounting brackets 24 of the base cutting block 12 and engages a posterior surface 90 of the mounting bracket 24 to secure the modular cutting block 14 to the base cutting block 12.

It should be appreciated that in other embodiments the retention mechanism may take other forms. For example, the arrangement of shafts and locking arms may be reversed with the base cutting block be configured to receive the shafts extending from the modular cutting blocks. In other embodiments, each modular cutting block may include a number of locking pins that may be extended and retracted to attach and detach the modular cutting block to the base cutting block. In still other embodiments, the retention mechanism may include an external latch on one block that engages a pin or flange on the block.

Figure 6:
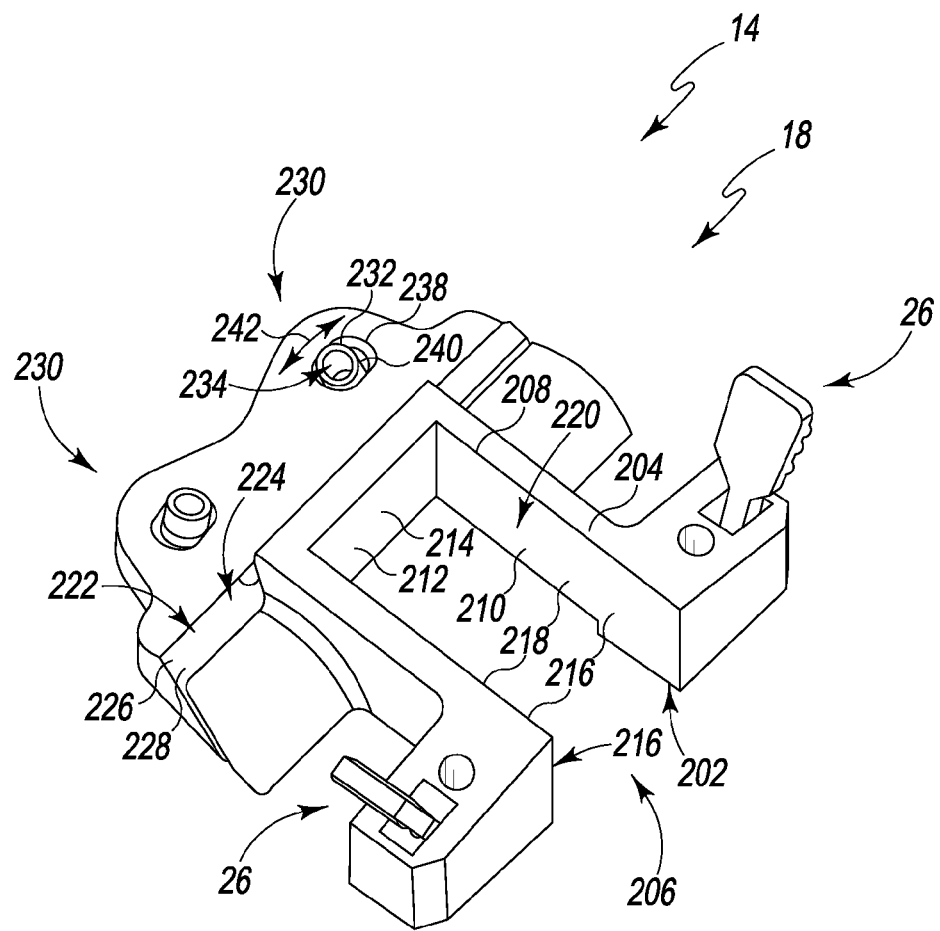
FIG. 6 is a perspective view of a notch cutting block of the instrument assembly of FIG. 1.

Referring now to FIG. 6, the modular cutting blocks 14 include a notch cutting block 18. The notch cutting block 18 includes a posterior side wall 202 that confronts the anterior side surface 82 of the base cutting block 12 when the notch cutting block 18 is secured to the block 12. The notch cutting block 18 also includes an anterior side wall 204 that is positioned opposite the posterior side wall 202. As described above, the notch cutting block 18 includes a pair of mounting brackets 26 of the retention mechanism 22, which are configured to secure the notch cutting block 18 to the base cutting block 12.

The notch cutting block 18 includes a notch cutting guide 206 that may be used during an orthopaedic surgical procedure to form a notch in the patient's femur sized to receive a femoral box of the femoral prosthetic component. As shown in FIG. 6, the notch cutting block 18 has an opening 208 defined in the anterior side wall 204, and an inner wall 210 extends posteriorly from the opening 208 to define the notch cutting guide 206 in the block 18. The inner wall 210 includes a planar surface 212 that defines a resection plane 214, which extends through a portion of the patient's femur when the notch cutting block 18 is secured to the base cutting block 12 on the patient's femur. In the illustrative embodiment, the resection plane 214 of the notch cutting guide 206 extends orthogonal to the resection planes 74 defined by the posterior cutting guides 68 of the base cutting block 12 when the notch cutting block 18 is secured to the block 12.

The inner wall 210 of the notch cutting block 18 also includes a pair of planar surfaces 216 that are connected to the planar surface 212 and extend transverse to the resection plane 214 defined by the surface 212. Each surface 216 defines a resection plane 218 that extends orthogonal to the resection planes 74 defined by the posterior cutting guides 68 of the base cutting block 12 when the notch cutting block 18 is secured to the block 12. The surfaces 212, 216 define a channel 220 of the notch cutting guide 206 sized to receive a surgical saw blade or other surgical instrument.

As shown in FIG. 6, the notch cutting block 18 also includes an anterior chamfer cutting guide 222. The anterior chamfer cutting guide 222 includes an elongated slot 224 that extends inwardly from an opening defined in the anterior side wall 204. The elongated slot 224 is sized to receive a cutting saw blade of a surgical saw or other surgical device. The cutting guide 222 includes a planar surface 226 that defines a resection plane 228. The resection plane 228 extends through an anterior portion of the patient's femur when the notch cutting block 18 is secured to the base cutting block 12 on the patient's femur. When the blocks 12, 18 are assembled, the resection plane 228 of the anterior chamfer cutting guide 222 extends obliquely relative to the resection planes 74 defined by the posterior cutting guides 68 such that an obtuse angle is defined between the planes 74, 228.

As shown in FIG. 6, a pair of fastener guides 230 are pivotally coupled to the notch cutting block 18. Each guide 230 includes a cylindrical body 232, and a bore 234 is defined in the body 232. The bore 234 is sized to receive fasteners such as, for example, fixation pins 58 (see FIG. 24), which may be utilized to secure the notch cutting block 18 to the patient's femur. It should be appreciated that in other embodiments the notch cutting block 18 may include additional fastener guides 230 or other fastening elements to secure the cutting block to the patient's femur.

Each cylindrical body 232 extends outwardly through a hole 238 defined in the anterior side wall 204 of the notch cutting block 18. Each fastener guide 230 also includes a hub 240 that is pivotally coupled to the block 18. In that way, the fastener guide 230 may be moved back and forth in the direction indicated by arrow 242 to adjust the orientation of the bore 234 and hence change the location of the fixation pin 58 on the patient's femur. It should be appreciated that in other embodiments the fixation guide 230 may be adjustable in other directions.

Figure 7:
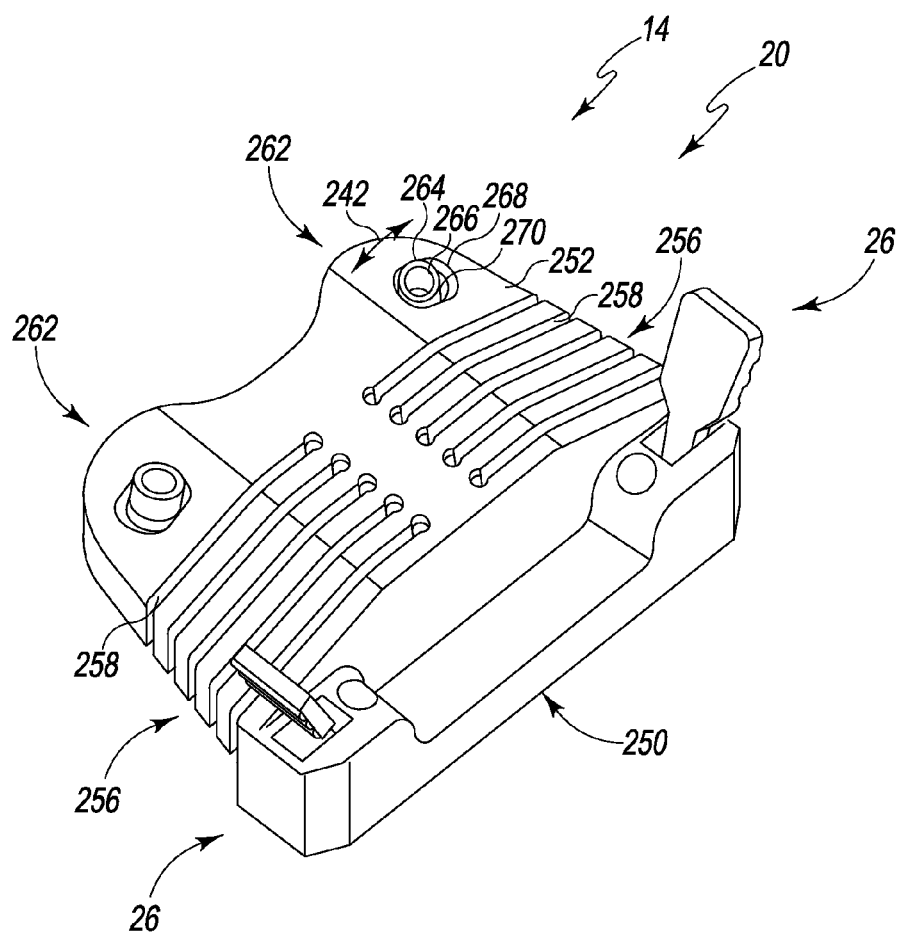
FIG. 7 is a perspective view of a distal cutting block of the instrument assembly of FIG. 1.

Referring now to FIG. 7, the modular cutting blocks 14 include a distal cutting block 20. The distal cutting block 20 includes a posterior side wall 250 that confronts the anterior side surface 82 of the base cutting block 12 when the distal cutting block 20 is secured to the block 12. The distal cutting block 20 also includes an anterior side wall 252 that is positioned opposite the posterior side wall 250. As described above, the distal cutting block 20 includes a pair of mounting brackets 26 of the retention mechanism 22, which are configured to secure the distal cutting block 20 to the base cutting block 12.

The distal cutting block 20 includes a number of distal cutting guides 256 that may be used during an orthopaedic surgical procedure to resect a distal portion of the patient's bone. Each cutting guide 256 includes an elongated slot sized to receive a cutting saw blade of a surgical saw or other surgical device. In the illustrative embodiment, the distal cutting block 20 has ten distal cutting guides 256 extending through the side walls 250, 252. Each distal cutting guide 256 includes a planar surface 258 that defines a resection plane 260. As shown in FIG. 7, the resection planes 260 of the cutting guides 256 extend parallel to, and are spaced from, each other. In the illustrative embodiment, the resection planes 260 of the distal cutting block 20 extends orthogonal to the resection planes 74 defined by the posterior cutting guides 68 of the base cutting block 12 when the distal cutting block 20 is secured to the block 12.

The resection planes 260 extend through a distal portion of the patient's femur when the distal cutting block 20 is secured to the base cutting block 12 on the femur. In that way, the cutting guides 256 may be used by the orthopaedic surgeon during the resection of the patient's femur. In the illustrative embodiment, the cutting guides 256 (hence the resection planes 260) are spaced part from each other by about four millimeters. As such, the surgeon may select the particular cutting guide 256 corresponding to the amount of bone to be removed. In other embodiments, the distal cutting block 20 may include any number of cutting guides 256, which may be spaced apart by an amount greater than or less than four millimeters.

As shown in FIG. 7, a pair of fastener guides 262 are pivotally coupled to the distal cutting block 20. Each guide 262 includes a cylindrical body 264, and a bore 266 is defined in the body 264. The bore 266 is sized to receive fasteners such as, for example, fixation pins 58 (see FIG. 26), which may be utilized to secure the distal cutting block 20 to the patient's femur. It should be appreciated that in other embodiments the distal cutting block 20 may include additional fastener guides 262 or other fastening elements to secure the cutting block to the patient's femur.

Each cylindrical body 264 extends outwardly through a hole 268 defined in the anterior side wall 252 of the distal cutting block 20. Each fastener guide 262 also includes a hub 270 that is pivotally coupled to the block 20. In that way, the fastener guide 262 may be moved back and forth in the direction indicated by arrow 272 to adjust the orientation of the bore 266 and hence change the location of the fixation pin 58 on the patient's femur. It should be appreciated that in other embodiments the fastener guide 262 may be adjustable in other directions.

Figure 8:
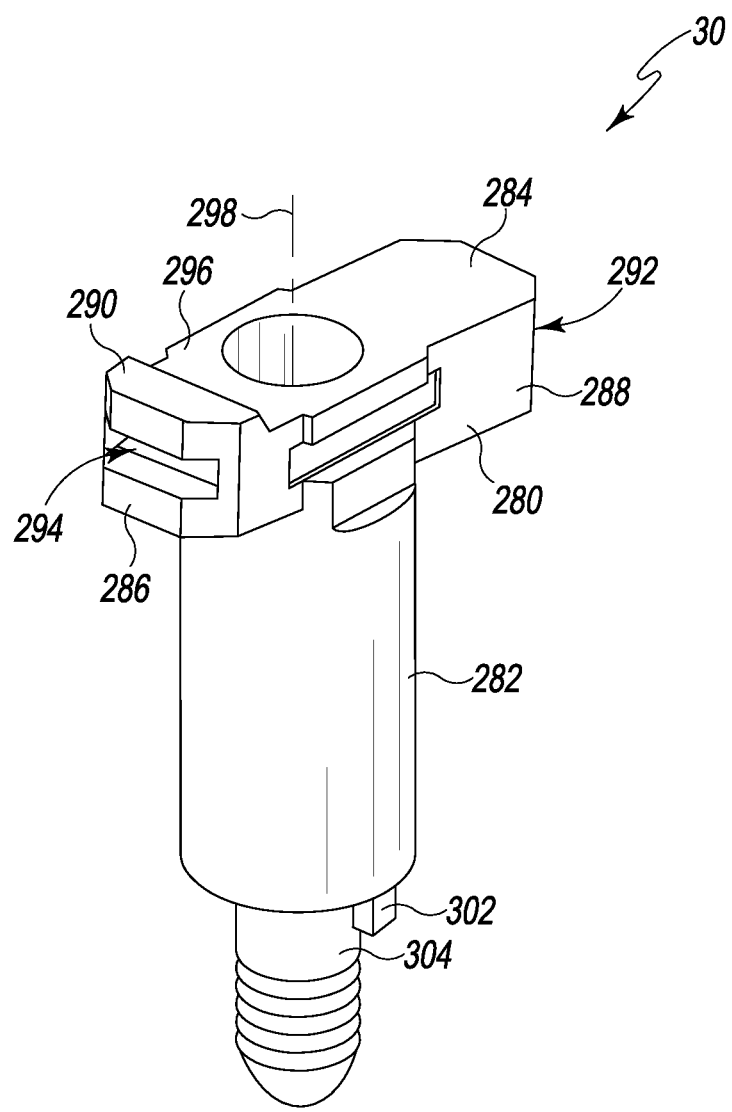
FIG. 8 is a perspective view of an intramedullary adaptor of the instrument assembly of FIG. 1.
Figure 9:
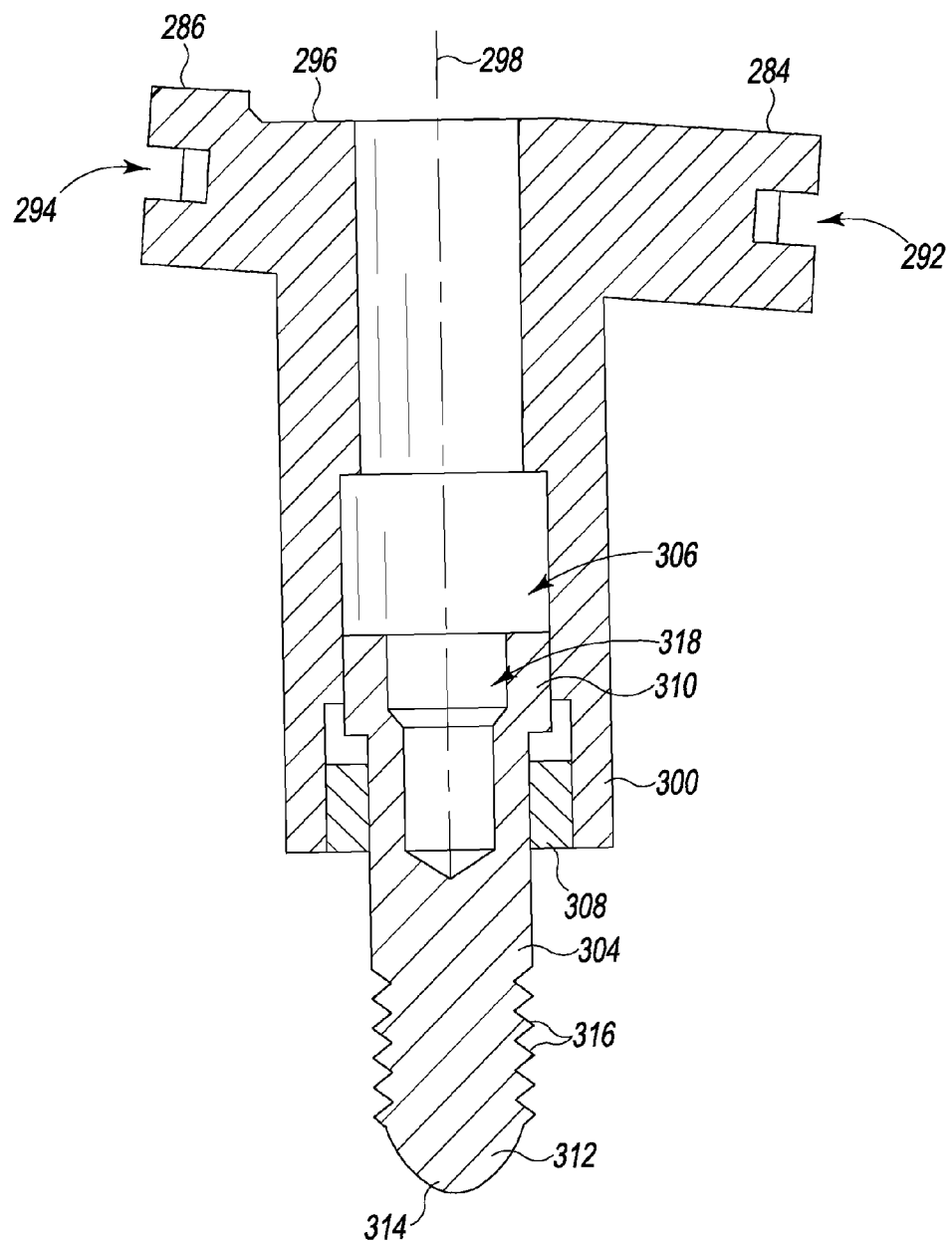
FIG. 9 is a cross-sectional side elevation view of the intramedullary adaptor of FIG. 8.

Referring now to FIGS. 8 and 9, the instrument assembly 10 includes an intramedullary adaptor 30 configured to be coupled to the base cutting block 12. The intramedullary adaptor 30 is formed from a metallic material, such as, for example, a stainless steel or a cobalt chromium alloy. The intramedullary adaptor 30 includes a mounting bracket 280 attached to a main body 282. As will be described in greater detail below, the mounting bracket 280 is sized to be positioned in the receiving slot 52 of the base cutting block 12. The mounting bracket 280 includes a pair of arms 284, 286 extending outwardly from the main body 282 to respective ends 288, 290. A channel 292 is defined in the end 288 of the arm 284, and the channel 292 is sized to receive the ear 114 of the locking tab 100 or the ear 126 of the locking tab 102 of the base cutting block 12. Another channel 294 is defined in the end 290 of the other arm 286. The channel 294 is also sized to receive the ear 114 of the locking tab 100 or the ear 126 of the locking tab 102 of the base cutting block 12.

As shown in FIG. 8, the mounting bracket 280 has a substantially planar distal surface 296. The main body 282 of the adaptor 30 has a longitudinal axis 298 that extends obliquely relative to the distal surface 296. The main body 282 has a proximal end 300, and a pair of alignment lugs 302 extend outwardly from the proximal end 300 of the body 282. The main body 282 is sized and shaped to be received in the medullary canal of the patient's femur, as described in greater detail below.

The adaptor 30 also includes a fastener 304 configured to secure the adaptor 30 to an intramedullary surgical instrument, as described in greater detail below. The fastener 304 is positioned in a passageway 306 defined in the body 282 and is configured to rotate relative to the main body 282. A retaining ring 308 is secured to the proximal end 300 of the main body 282, thereby securing the fastener 304 to the main body 282.

Referring now to FIG. 9, the fastener 304 includes a head 310 positioned in the passageway 306 and a shaft 312 extending through the retaining ring 308 and outwardly from the body 282 to a proximal end 314. The proximal end 314 of the shaft 312 has a plurality of external threads 316 formed thereon. The head 310 of the fastener 304 has a socket 318 defined therein. In an orthopaedic surgical procedure, a surgeon may insert the surgical tool into the socket 318 to rotate the fastener 304 relative to the main body 282.

Figure 10:
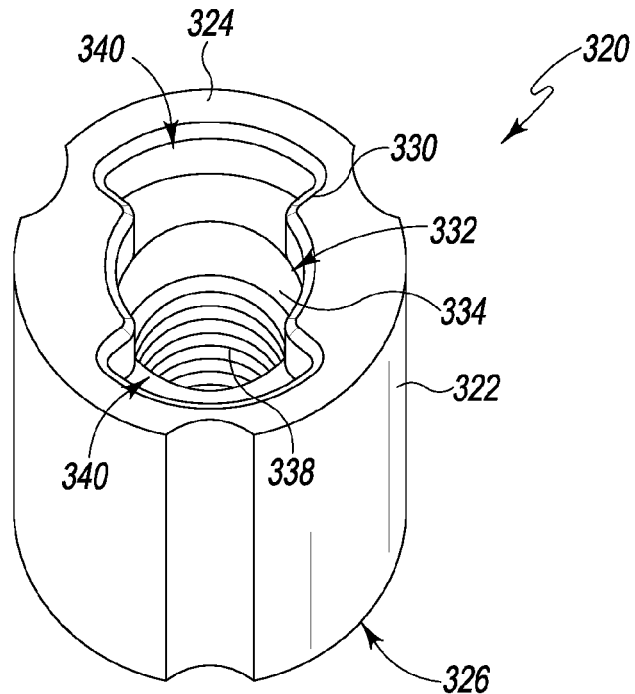
FIG. 10 is a perspective view of one embodiment of a stem stabilizer configured to be coupled to the intramedullary adaptor of FIG. 8.
Figure 11:
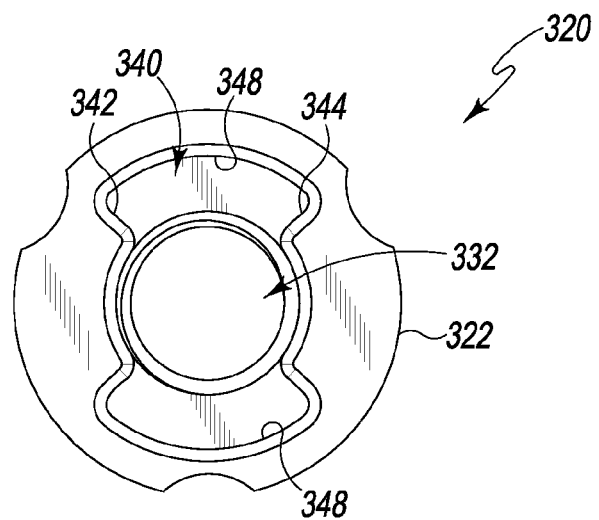
FIG. 11 is plan view of the stem stabilizer of FIG. 10.

Referring now to FIGS. 10-18, a number of other surgical instruments for use with the instrument assembly 10 are shown. In FIGS. 10 and 11, one embodiment of a stem stabilizer 320 is shown. The stem stabilizer 320 is formed from a metallic material, such as, for example, a stainless steel or a cobalt chromium alloy. The stem stabilizer 320 includes a cylindrical body 322 extending from an end 324 configured to confront the proximal end 300 of the main body 282 of the adaptor 30 to an end 326 configured to confront the distal end of a stem trial 328 (see FIG. 20). The end 324 of the body 322 has an opening 330 defined therein, and a central passageway 332 extends inwardly from the opening 330 through the body 322. The central passageway 332 is sized to receive the shaft 312 of the intramedullary adaptor 30. A cylindrical inner wall 334 defines the passageway 332, and the inner wall 334 has a plurality of internal threads 338 formed thereon that correspond to the external threads 316 formed on the shaft 312 and the external threads (not shown) formed on the stem trial 328. When the stem trial 328 is secured to the stem stabilizer 320, an intramedullary orthopaedic surgical instrument 336 is formed (see FIG. 20), as described in greater detail below.

As shown in FIG. 11, a pair of slots 340 extend inwardly from the opening 330 on either side of the central passageway 332. Each slot 340 is arcuate in shape and is defined by a pair of substantially planar inner walls 342, 344 and an arcuate inner wall 346 extending between the inner walls 342, 344. As will be described in greater detail below, one alignment lug 302 of the intramedullary adaptor 30 is positioned in each arcuate slot 340 when the intramedullary adaptor 30 is secured to the stem stabilizer 320.

Each arcuate inner wall 346 defines an arc 348. The magnitude of the arc 348 is dependant on the permitted rotation of the femoral prosthetic component and therefore varies depending on the choice of prosthetic component.

Figure 12:
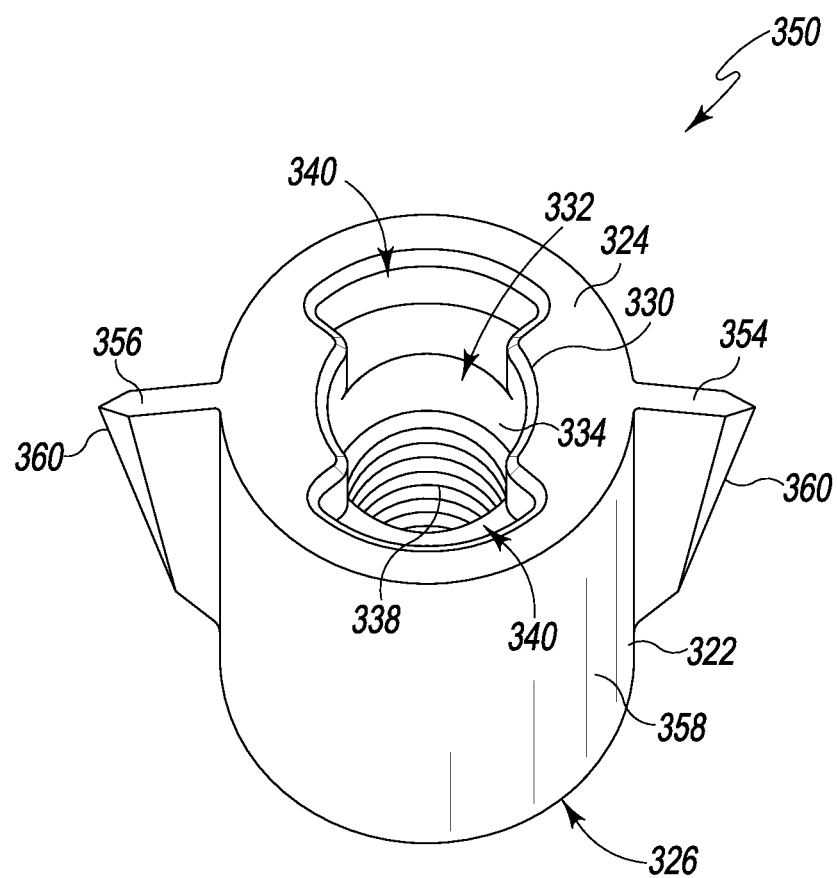
FIG. 12 is a perspective view of another embodiment of a stem stabilizer configured to be coupled to the intramedullary adaptor of FIG. 8.

Referring now to FIG. 12, another embodiment of a stem stabilizer (hereinafter stem stabilizer 350) is shown. The stem stabilizer 350 includes a cylindrical body 352 extending from an end 324 configured to confront the proximal end 300 of the main body 282 of the adaptor 30 to an end 326 configured to confront the distal end of a stem trial 328 (see FIG. 20). A medial fin 354 and a lateral fin 356 extend outwardly from an outer surface 358 of the cylindrical body 352. Each of the fins 354, 356 includes an outer edge 360 configured to engage the patient's femur when the stem stabilizer 350 is positioned in the medullary canal. In that way, the fins 354, 356 may provide additional stability during an orthopaedic surgical procedure. It should be appreciated that in other embodiments the stem stabilizer may include additional fins having different sizes and different configurations.

Like the stem stabilizer 350, the end 324 of the body 352 has an opening 330 defined therein, and a central passageway 332 extends inwardly from the opening 330 through the body 352. The central passageway 332 is sized to receive the shaft 312 of the intramedullary adaptor 30. A cylindrical inner wall 334 defines the passageway 332, and the inner wall 334 has a plurality of internal threads 338 formed thereon that correspond to the external threads 316 formed on the shaft 312. A pair of arcuate slots 340 extend inwardly from the opening 330 on either side of the central passageway 332.

Figure 13:
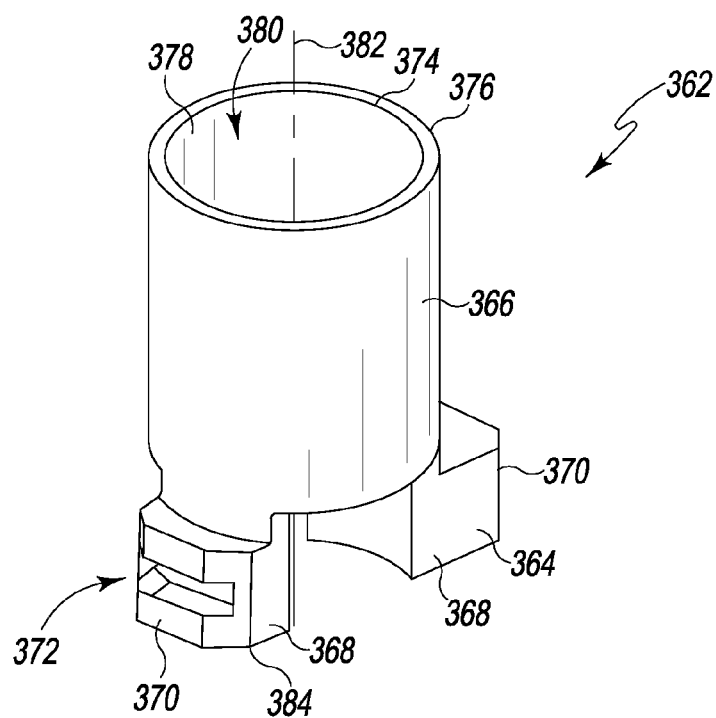
FIG. 13 is a perspective view of one embodiment of a guide block configured to be coupled to the base cutting block of FIG. 2.

Referring now to FIG. 13, a guide block 362 is shown. The guide block 362 is configured to be secured to the base cutting block 12 in place of the intramedullary adaptor 30. The guide block 362 is formed from a metallic material, such as, for example, a stainless steel or a cobalt chromium alloy. The guide block 362 includes a mounting bracket 364 attached to a bushing 366. As will be described in greater detail below, the mounting bracket 364 is sized to be positioned in the receiving slot 52 of the base cutting block 12. The mounting bracket 364 includes a pair of arms 368 extending outwardly from the bushing 366 to respective ends 370. A channel 372 is defined in each end 370 of the arm 368. The channel 372 is sized to receive the ear 114 of the locking tab 100 or the ear 126 of the locking tab 102 of the base cutting block 12.

The bushing 366 of the guide block 362 has an opening 374 defined in a distal end 376 thereof. A cylindrical inner wall 378 extends inwardly from the distal end 376 to define a passageway 380 through the bushing 366. The passageway 380 is sized to permit the passage of a surgical drill or reamer. In that way, the block 362 guides the surgical drill or reamer during the orthopaedic surgical procedure.

As shown in FIG. 13, the passageway 380 has a longitudinal axis 382. The mounting bracket 364 has a substantially planar distal surface 384. In the illustrative embodiment, an oblique angle is defined between the longitudinal axis 382 and the substantially planar proximal surface 384.

Figure 14:
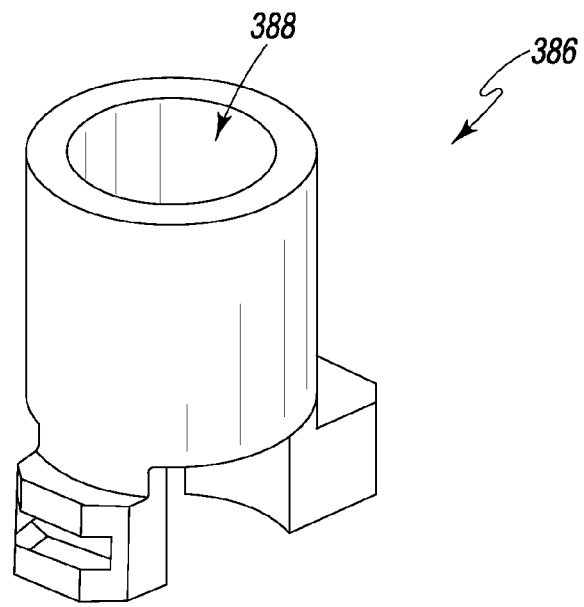
FIG. 14 is a perspective view of another embodiment of a guide block configured to be coupled to the base cutting block of FIG. 2.

It should be appreciated that in other embodiments the passageway 380 of the guide block 362 may be resized to accommodate various types of surgical drills or reamers. For example, as shown in FIG. 14, another embodiment of a guide block 386 includes a passageway 388 that has a smaller diameter than the passageway 380. Additionally, the angle defined between the longitudinal axis of the passageway and the distal surface 384 of the mounting bracket 364 may also vary. In other embodiments, the length of the bushing may also vary.

Figure 15:
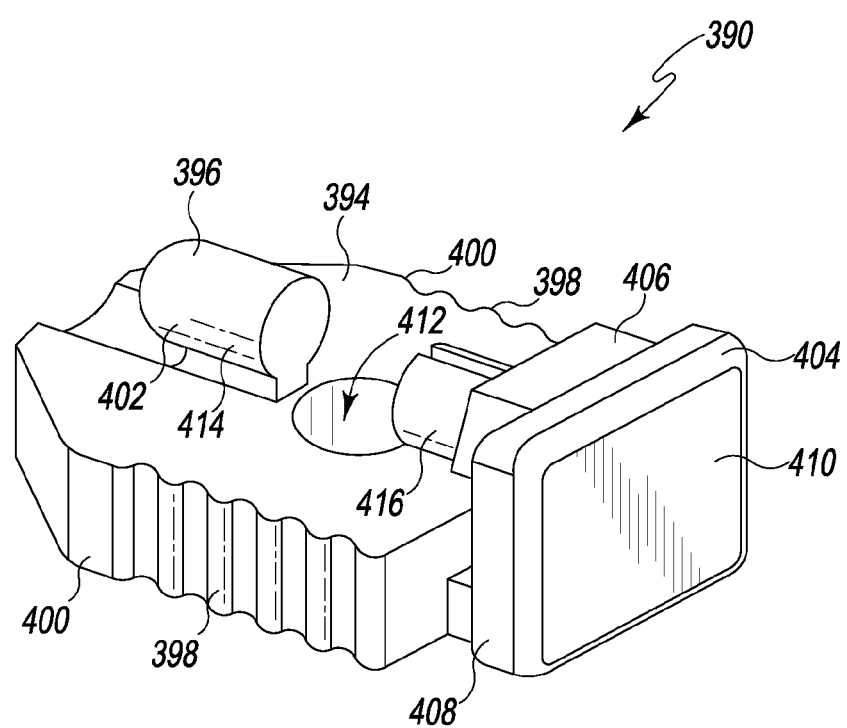
FIG. 15 is a perspective view of a distal spacer block configured to be coupled to the base cutting block of FIG. 2.

Referring now to FIG. 15, a distal spacer block 390 is shown. The block 390 is configured to be secured to base cutting block 12 between the proximal surface 46 of the plate 40 and a distal end of the patient's femur. The distal spacer block 390 is formed from a metallic material, such as, for example, a stainless steel or a cobalt chromium alloy. The spacer block 390 may be one of a plurality of spacer blocks having different sizes and corresponding to different prosthetic augment sizes.

The block 390 includes a plate 394 and a pin 396 secured to the plate 394. The plate 394 includes pair of grips 398 formed on each side 400 thereof. A surgeon may grasp the grips 398 to insert the block 390 between the base cutting block 12 and the patient's femur. As shown in FIG. 5, the pin 396 of distal spacer block 390 includes a cylindrical shaft 402 sized to be received in the channel 138 defined in the base cutting block 12. The shaft 402 has an outer diameter that is greater than the inner diameter of the cylindrical segment 140 of the channel 138 such that the distal spacer block 390 is secured to the base cutting block 12 via friction.

The distal spacer block 390 also includes a stop 404 secured to the plate 394. The stop 404 includes a flange 406 that confronts one of the side wall 132, 144 of the base cutting block 12 when the distal spacer block 390 is properly positioned. The stop 404 also includes a grip 408, which the surgeon may use to withdraw the block 390 from between the base cutting block 12 and the patient's femur. An indicator (not shown) may be etched into the outer surface 410 of the stop 404 to indicate the size of the spacer block 390.

The spacer block 390 also includes a bore 412 that is defined in the plate 394. As shown in FIG. 15, the bore 412 divides the pin 396 into two sections 414, 416. When the distal spacer block 390 is properly positioned, the bore 412 is axially aligned with the guide bore 56 of the fastener guide 54. When a fixation pin 58 is inserted into the fastener guide 54 while the distal spacer block 390 is secured to the base cutting block 12, the pin 58 is advanced through the guide bore 56 and the bore 412 into the patient's femur.

Figures 16, 17:
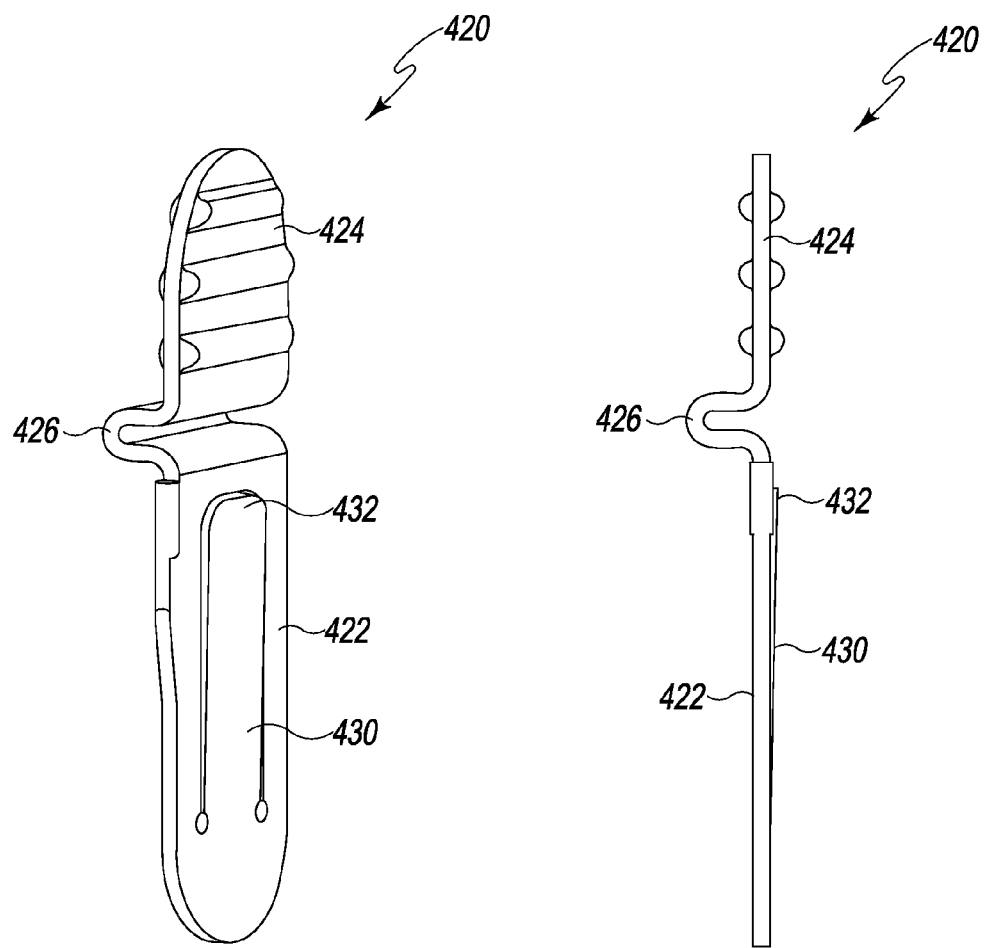
FIG. 16 is a perspective view of a shim configured to be coupled to the base cutting block of FIG. 2.
FIG. 17 is a side elevation view of the shim of FIG. 16.

Referring now to FIGS. 16 and 17, a posterior shim 420 is shown. The posterior shim 420 is configured to be positioned in one of the cutting guides 68 defined in the base cutting block 12 during a surgical procedure. The posterior shim 420 is formed from a metallic material, such as, for example, a stainless steel or a cobalt chromium alloy. The posterior shim 420 includes a body 422 sized to be positioned in a cutting guide 68 and a grip 424 that may be grasped by the surgeon to position the posterior shim 420 in the cutting guide 68.

The posterior shim 420 also includes a stop 426 positioned between the body 422 and the grip 424. The stop 426 includes a flange 428 that confronts the articulating surface 62 of one of the arms 42 of the base cutting block 12. A cantilevered spring 430 is secured to the body 422 of the posterior shim 420. The cantilevered end 432 of the spring 430 is configured to engage the side walls of the cutting guide 68 to retain the posterior shim 420 in position.

Figure 18:
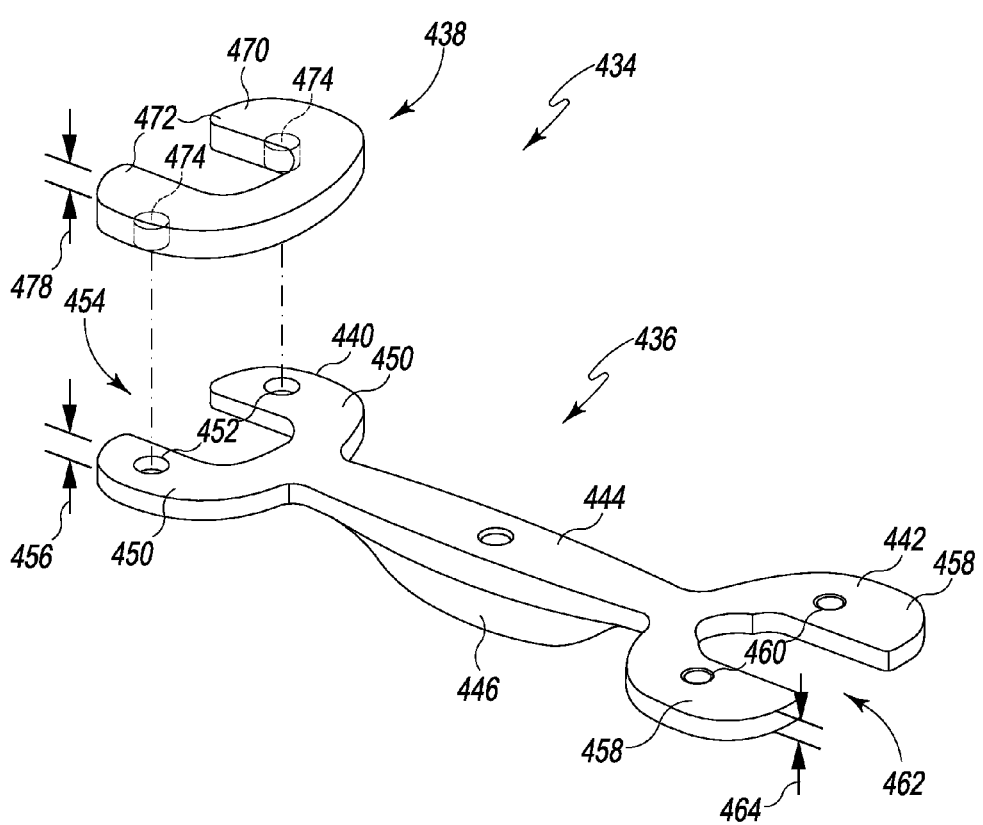
FIG. 18 is a perspective view of a gap assessment tool.

Referring now to FIG. 18, a gap assessment tool 434 is shown. The gap assessment tool 434 includes a handle 436 and a plurality of shim blocks 438 configured to be secured to the handle 436. Only a single shim block 438 is shown in FIG. 18. The handle 436 has a spacer end 440, a spacer end 442 positioned opposite the spacer end 440, and a body 444 connecting the ends 440, 442. The handle 436 is formed from a metallic material, such as, for example, a stainless steel or a cobalt chromium alloy. It should also be appreciated that the handle 436 may be formed from a hard polymeric material. The body 444 includes a grip 446 that may be utilized by the surgeon to manipulate the handle 436.

The spacer end 440 includes a pair of arms 450 extending outwardly from the body 444 of the handle 436. Each arm 450 has a bore 452 defined therein, and an opening 454 is defined between the arms 450. The spacer end 440 has a thickness 456 that corresponds to the thickness of a tibial trial. Similarly, the spacer end 442 also includes a pair of arms 458 extending outwardly from the body 444 of the handle 436. Each arm 458 has a bore 460 defined therein, and an opening 462 is defined between the arms 458. The spacer end 442 has a thickness 464 that corresponds to the thickness of another tibial trial. In the illustrative embodiment, the thicknesses 456, 464 of the spacer ends 440, 442 are different.

Each shim block 438 includes an articulation surface 470 configured to engage the articulating surface 62 of the base cutting block 12. The shim blocks 438 are formed from a hard polymeric material, such as, for example, acetal. It should be appreciated that in other embodiments the blocks 438 may be formed from a metallic material, such as, for example, stainless steel or cobalt chromium. The shim block 438 has a pair of arms 472 that correspond to the arms 450, 458 of the handle 436. Each arm 472 has a post 474 extending downwardly from a bottom surface 476. Each post 474 is sized to be received in each bore 452, 460 defined in the handle 436. The shim block 438 may include a spring or other retention device to secure the shim block 438 to the handle 436.

As described above, the gap assessment tool 434 includes a plurality of shim blocks 438, each of which may be separately attached to the handle 436. Each shim block 438 has a different thickness 478 such that the surgeon is able to assemble a gap assessment tool of one size and configuration, evaluate the performance, and then modify the gap assessment tool as necessary to determine intraoperatively the flexion and extension gaps of the patient, as described in greater detail below.

Returning to FIG. 1, the instrument assembly 10 also includes a cover 28 configured to be positioned over the shafts 84 of the base cutting block. The cover 28 has a body 480 that includes a substantially planar posterior surface 482. In the illustrative embodiment, the body 480 is formed from a polymeric material, such as, for example, acetal. It should be appreciated that in other embodiments the cover may be formed from a metallic material.

The posterior surface 482 of the cover 28 confronts the anterior side surface 82 of the base cutting block 12 when the cover 28 is secured thereto. A pair of openings 484 are defined in the posterior surface 482. The openings 484 are sized and positioned to receive the shafts 84 of the base cutting block 12. The cover 28 also includes a pair of grips 488 defined on sides 490 of the body 480. A surgeon may use the grips 488 to align the cover 28 with the base cutting block 12 and then advance the cover 28 over the shafts 84.

Figure 19A:
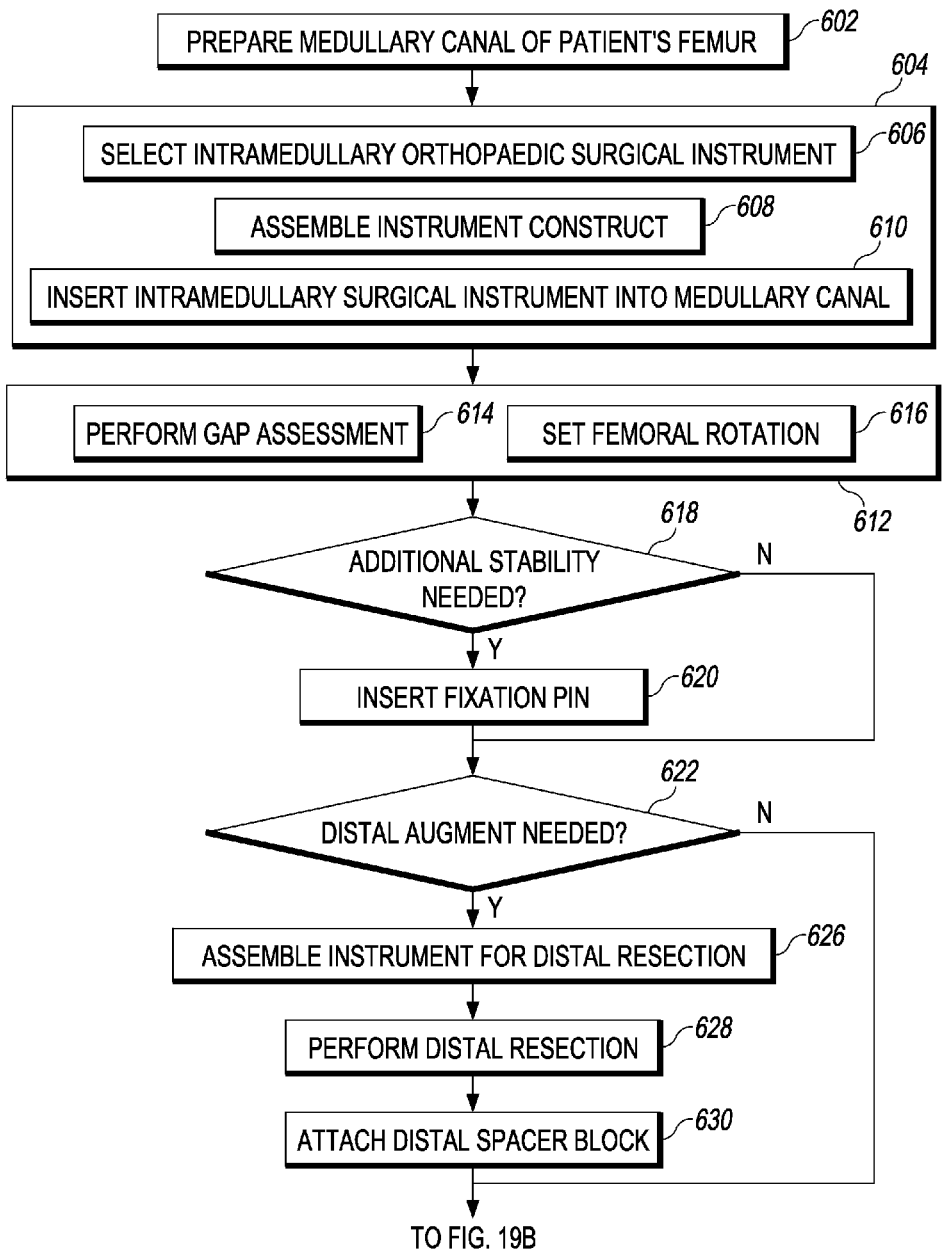
FIGS. 19A and 19B are a simplified flow chart of a procedure for using the orthopaedic surgical instruments of FIGS. 1-18.
Figure 19B:
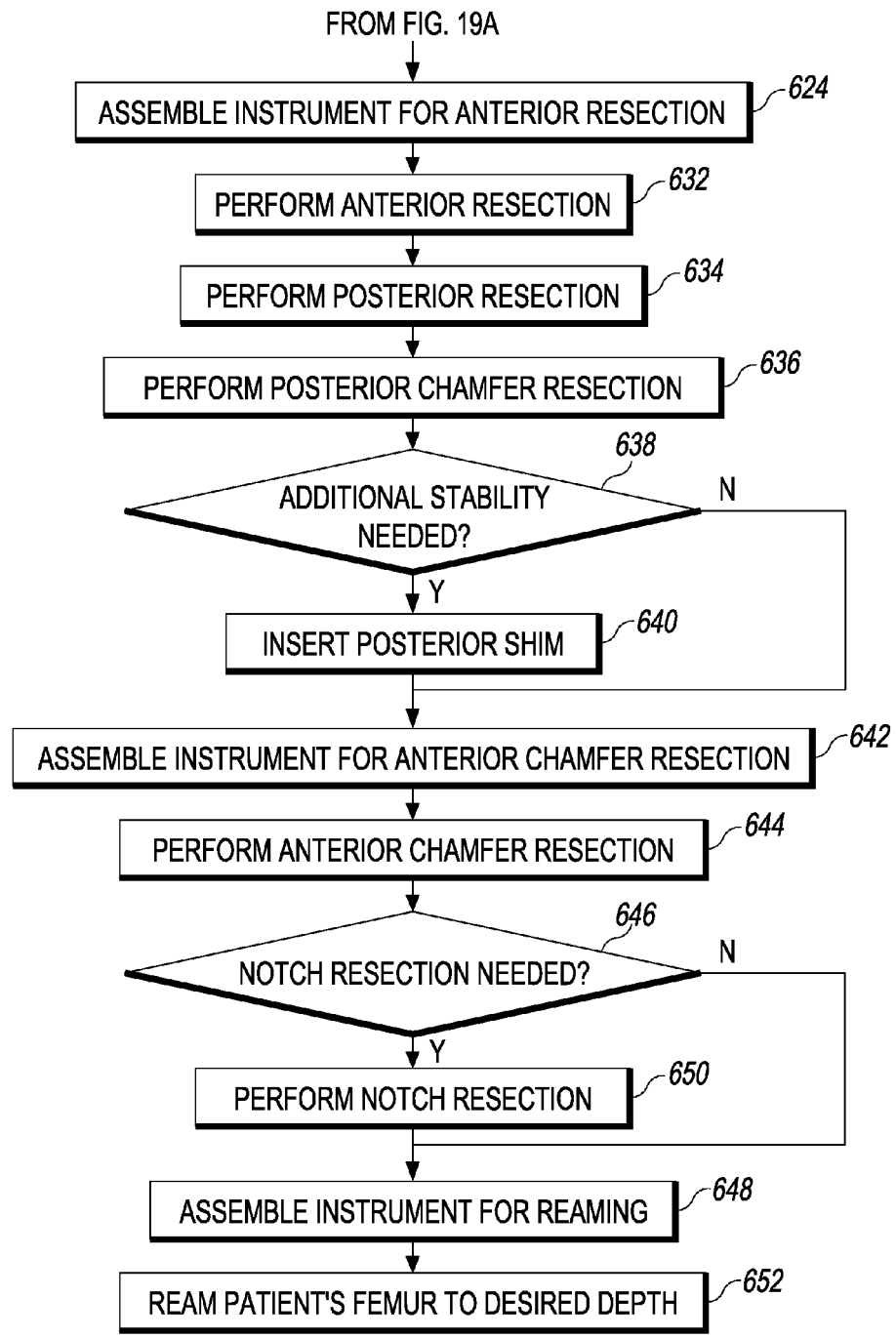

The assembly 10 may be utilized during the performance of an orthopaedic surgical procedure similar to that shown in FIGS. 19A and 19B. As shown in FIGS. 20-23, an orthopaedic instrument construct 500 is formed from the intramedullary orthopaedic surgical instrument 336, the intramedullary adaptor 30, and the base cutting block 12. The orthopaedic instrument construct 500 is attached to a distal end 502 of a patient's femur 504, with the intramedullary orthopaedic surgical instrument 336 and the proximal end 314 of the intramedullary adaptor 30 positioned in the medullary canal 506 of the patient's femur 504. A gap assessment may then be performed and femoral rotation set.

As shown in FIGS. 24-32, various modular cutting block 14 may be separately secured to the base cutting block 12 (with and without the intramedullary orthopaedic surgical instrument 336 and the intramedullary adaptor 30 secured thereto). Each cutting block 14 may be used to resect portions of the distal end 502 of the patient's femur 504. A guide block 362 may be attached to the base cutting block 12 to guide, for example, a surgical drill used to ream the medullary canal 506.

Referring now to FIGS. 19A and 19B, an illustrative orthopaedic surgical procedure 600 utilizing the assembly 10 is shown. In procedure block 602, the medullary canal 506 of the patient's femur 504 is initially prepared. To do so, an orthopaedic surgeon may drill and/or ream the medullary canal 506 to receive the intramedullary orthopaedic surgical instrument 336. Multiple drills or reamers may be used to increase the size of opening 510 of the medullary canal 506 of the patient's femur 504.

After preparing the medullary canal 506 of the patient's femur 504, the surgeon may assemble the instrument construct 500 and insert the intramedullary orthopaedic surgical instrument 336 into the medullary canal 506 in procedure block 604. To do so, the surgeon may select the intramedullary orthopaedic surgical instrument 336 from a plurality of intramedullary orthopaedic surgical instrument 336. For example, the surgeon may select a stem trial 328 and a stem stabilizer 320, 350 from a plurality of stem trials 328 and a plurality of stem stabilizers 320, 350. The stem trials 328 may vary in length, diameter, or other aspect, and the surgeon selects the stem trial 328 based on the patient's anatomy and the type of prosthetic stem component to be included in the femoral prosthesis. Similarly, the stem stabilizer may be selected based on the patient's anatomy and whether additional stability may be needed in the medullary canal 506. When the surgeon has selected an appropriate stem trial 328 and stem stabilizer 320, 350, the surgeon may thread the stem trial 328 onto the proximal end 326 of the stem stabilizer 350 to form the intramedullary orthopaedic surgical instrument 336 shown in FIG. 20.

It should also be appreciated that in other embodiments the stem trials and stem stabilizers may be formed as single, monolithic units of different sizes and configurations. It should also be appreciated that in other embodiments the intramedullary orthopaedic surgical instrument 336 may take the form of a femoral broach having a plurality of teeth configured to engage the patient's femur 504 when inserted into the medullary canal 506.

After selecting the intramedullary orthopaedic surgical instrument, the surgeon may assemble the instrument construct 500 in procedure block 608. To do so, the surgeon may align the end 324 of the stem stabilizer 350 with the fastener 304 of the intramedullary adaptor 30. The threaded shaft 312 of the fastener 304 may be advanced into engagement with the threaded inner wall 334 of the stem stabilizer 350. A surgeon may use a driver or other surgical tool to rotate the fastener 304 to thread the shaft 312 into the stem stabilizer 350, thereby securing the intramedullary adaptor 30 to the intramedullary orthopaedic surgical instrument 336. When the adaptor 30 is secured to the instrument 336, the alignment lugs 302 of the adaptor 30 are positioned arcuate slots 340 of the stem stabilizer 350.

The intramedullary adaptor 30 may be then attached to the base cutting block 12. To do so, the mounting bracket 280 of the adaptor 30 is positioned in the receiving slot 52 of the base cutting block 12. A surgeon may use a driver or other surgical tool to rotate the locking tabs 100, 102 about respective axes 112, 124 as indicated by arrows 512 in FIG. 20. As the locking tabs 100, 102 rotate, the ears 114, 126 are advanced into the channels 292, 294 defined in the mounting bracket 280, thereby securing the adaptor 30 to the block 12 and forming the instrument construct 500 shown in FIG. 20. The surgeon may choose to attach the adaptor 30 to the base cutting block 12 before attaching the intramedullary orthopaedic surgical instrument 336 to the adaptor 30.

Figure 20:
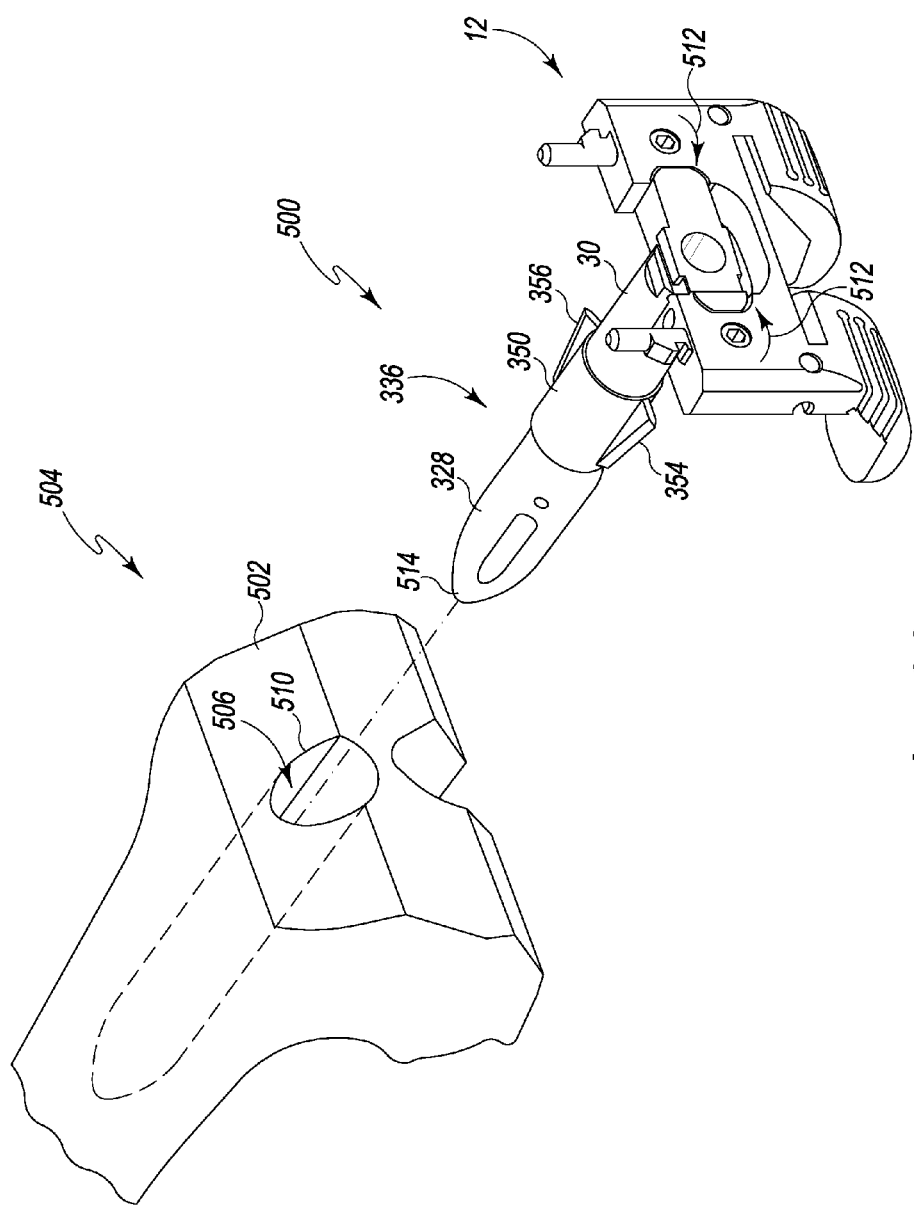
FIGS. 20-32 are views of a patient's femur and the orthopaedic surgical instruments of FIGS. 1-18 as the orthopaedic surgical instruments are used in the procedure of FIG. 19.

After the instrument construct 500 is assembled, the surgeon may insert the intramedullary orthopaedic surgical instrument 336 into the medullary canal 506 in procedure block 610. To do so, the surgeon aligns the end 514 of the intramedullary orthopaedic surgical instrument 336 with the opening 510 of the medullary canal 506 as shown in FIG. 20. The surgeon may advance the instrument construct 500 such that the intramedullary orthopaedic surgical instrument 336 advances through the opening 510 and into the medullary canal 506. The fins 354, 356 of the stem stabilizer 350 are moved into engagement with the femur 504. A mallet or other surgical tool may be used to fully insert the intramedullary orthopaedic surgical instrument 336 in the medullary canal 506 and seat the base cutting block 12 on the distal end 502 of the patient's femur 504. It should also be appreciated that in other embodiments the intramedullary orthopaedic surgical instrument 336 may be positioned in the medullary canal 506 prior to attachment to the adaptor 30.

After the intramedullary orthopaedic surgical instrument 336 is positioned in the medullary canal 506 and the base cutting block 12 on the distal end 502 of the patient's femur 504, the surgeon may adjust the base cutting block 12 on the distal end 502 in procedure block 612. To do so, the surgeon may insert a driver or other surgical tool into the socket 318 defined in the fastener 304 of the intramedullary adaptor 30 to loosen the connection between the adaptor 30 and the intramedullary orthopaedic surgical instrument 336. In that way, the adaptor 30 and the base cutting block 12 are permitted to rotate relative to the intramedullary orthopaedic surgical instrument 336. The surgeon also attached the cover 28 to the base cutting block 12 to cover the exposed shafts 84.

To adjust the base cutting block 12, the surgeon performs a gap assessment in procedure block 614 and sets the femoral rotation of the base cutting block 12 in procedure block 616. It should be appreciated that blocks 614, 616 may be performed in any order.

Figure 21:
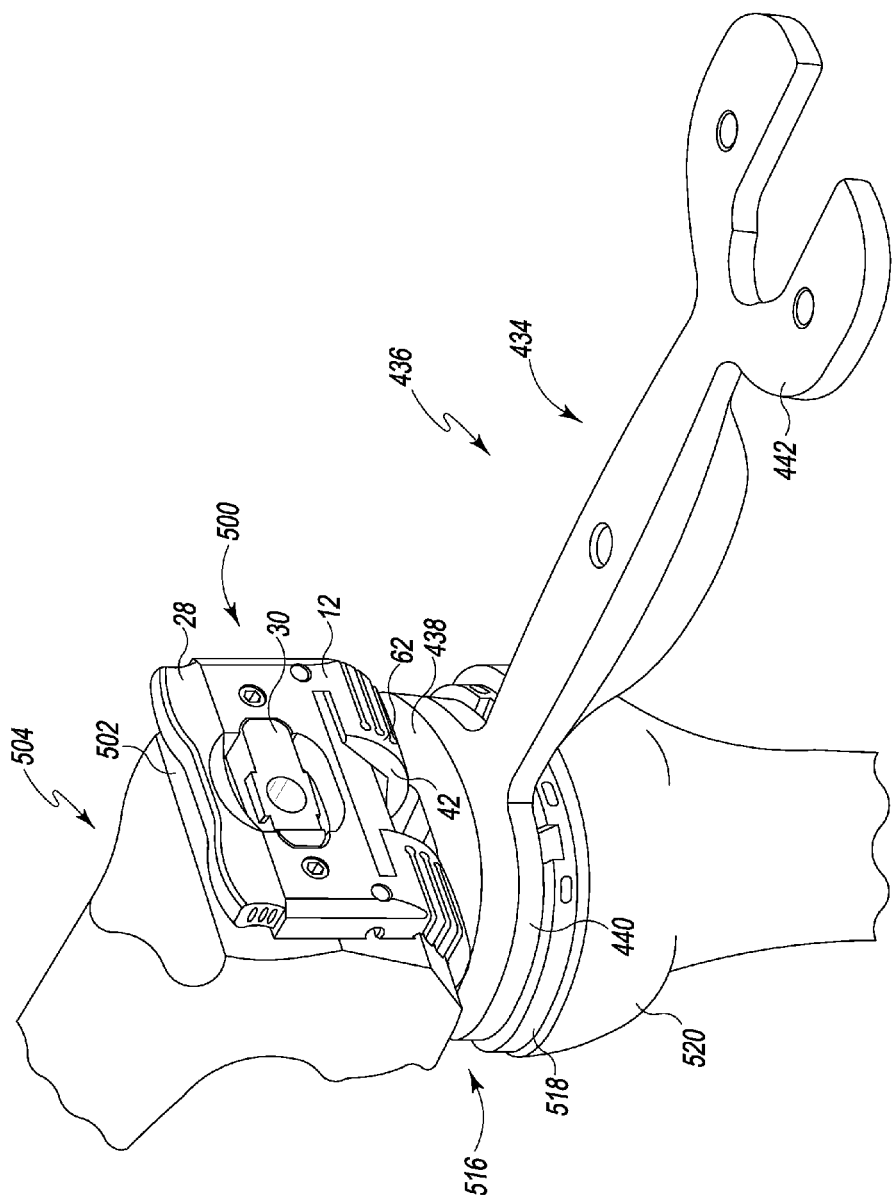
Figure 22:
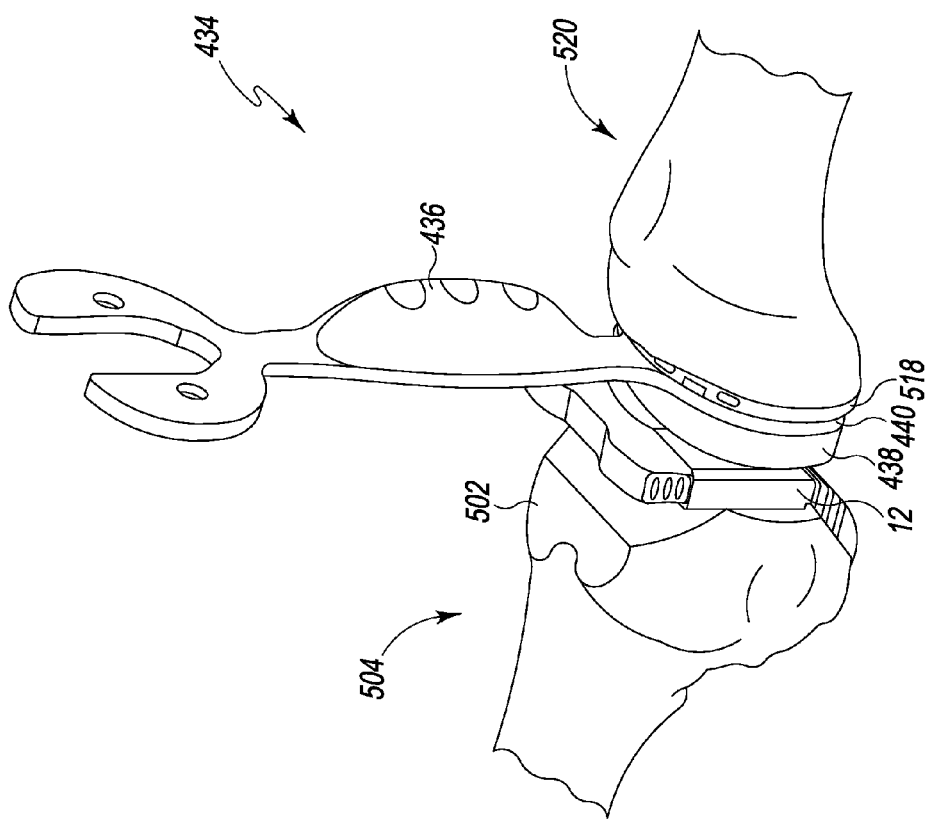

In procedure block 614, the surgeon assesses the flexion and extension gaps through the range of motion. To do so, the surgeon selects a gap assessment tool 434. The surgeon may use only the handle 436 and one of the spacer ends 440, 442 having a desired thickness. Alternatively, the surgeon may select a shim block 438. As shown in FIG. 21, the surgeon may attach the shim block 438 to one of the spacer ends 440, 442 of the handle 436 to assemble the gap assessment tool 434.

As shown in FIG. 21, a gap 516 is defined between the base cutting block 12 and a tibial trial component 518 attached to a patient's tibia 520. With the patient's knee in flexion as shown in FIG. 21, the surgeon may insert the gap assessment tool 434 into the gap 516. The surgeon may move the knee between flexion (FIG. 21) and extension (FIG. 22) to evaluate the gap 516 and the stability of the construct throughout the range of motion. The surgeon may substitute one shim block 438 for a shim block of different thickness to achieve the desired gap geometry. It should be appreciated that in other embodiments the gap assessment may be performed with another type of tensioning device, such as, for example, a laminar spreader.

Figure 23:
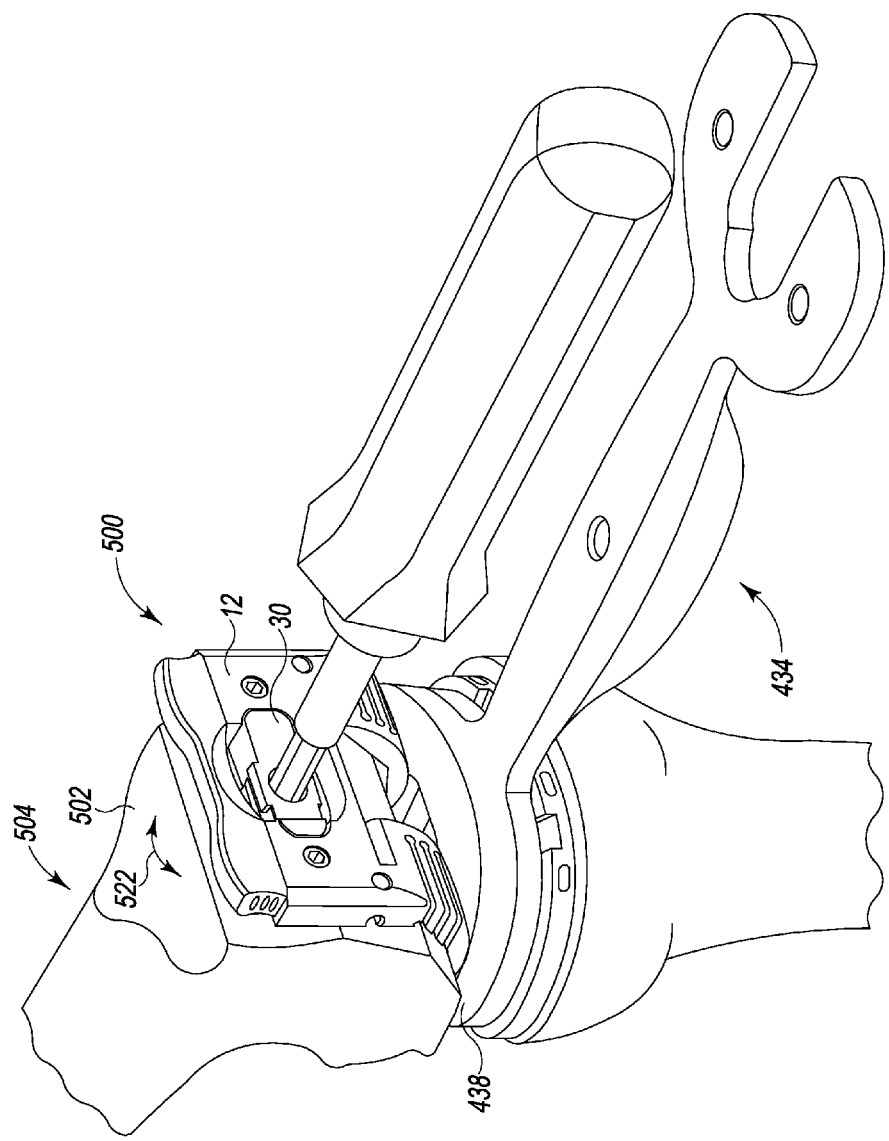

In procedure block 616, the surgeon sets the femoral rotation of the base cutting block 12. To do so, the surgeon may balance the base cutting block 12 parallel to the tibial trial component 518 at 90 degrees of flexion as shown in FIG. 23. The surgeon may grasp the side walls 132, 144 of the base cutting block 12 to rotate the base cutting block 12 in the direction indicated by arrow 522 until the gap 516 defined between the base cutting block 12 and the tibial trial component 518 is rectangular. As the base cutting block 12 is rotated, the alignment lugs 302 of the adaptor 30 are advanced along the slots 340 of the stem stabilizer 350. Engagement between the alignment lugs 302 and the planar inner walls 342, 344 of the stem stabilizer 350 prevents the surgeon from rotating the base cutting block 12 beyond a predetermined angle. When the base cutting block 12 is balanced, the surgeon may a driver or other surgical tool to rotate the fastener 304 to secure the intramedullary adaptor 30 to the intramedullary orthopaedic surgical instrument 336, thereby preventing relative movement between the adaptor 30 and the base cutting block 12 and the instrument 336.

Alternatively, the surgeon may set the femoral rotation by inserting two Steinman pins (not shown) into the channels 138 defined in the side wall 132, 144 of the base cutting block 12. With the Steinman pins extending outwardly from the block 12, the surgeon may orient the block 12 referencing the medial and lateral epicondyles. When the base cutting block 12 is properly position, the surgeon may rotate the fastener 304 to secure the intramedullary adaptor 30 to the intramedullary orthopaedic surgical instrument 336.

Figure 24:
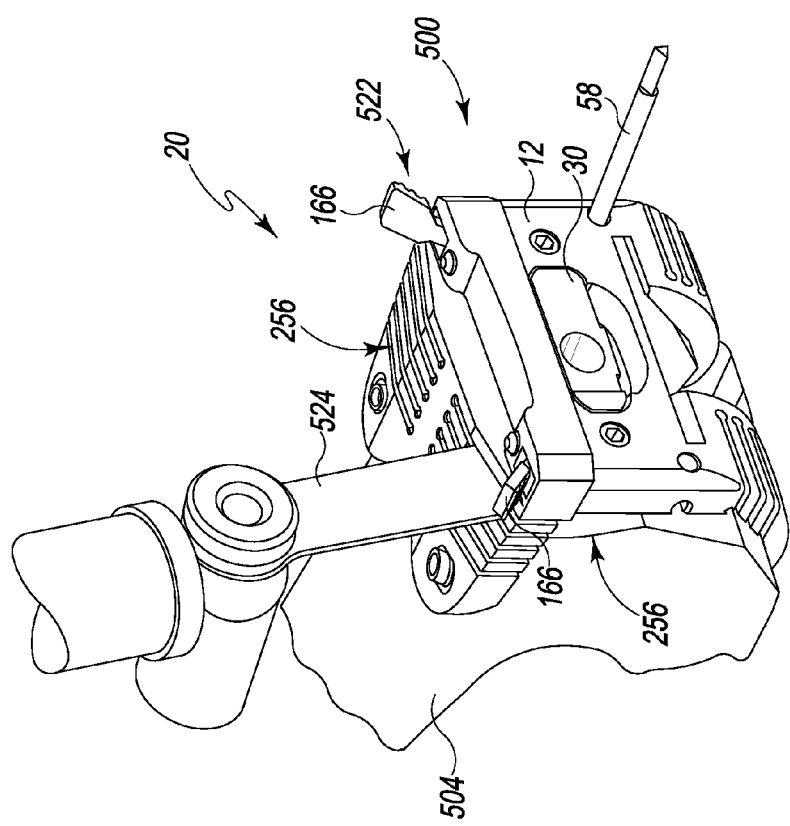

Returning to FIG. 19A, the procedure 600 may proceed to procedure block 618 in which the surgeon determines if the instrument construct 500 requires additional stability. If the surgeon decides additional stability is needed, the procedure 600 advances to procedure block 620 in which a fixation pin 58 is inserted into a fastener guide 54 of the base cutting block 12, as shown in FIG. 24. One or more fixation pins may be used to further secure the base cutting block 12 to the distal end 502 of the patient's femur 504. The procedure 600 may then proceed to procedure block 622.

If the surgeon determines in procedure block 618 that the instrument construct 500 is sufficiently stable on the distal end 502 of the patient's femur 504, the procedure 600 proceeds to procedure block 622 in which the surgeon determines whether the femoral prosthesis requires a prosthetic augment component. The surgeon may make that determination based on the gap assessment performed in procedure block 614. If the surgeon determines that an augment component is unnecessary, the procedure advances to procedure block 624. If an augment component is required, the procedure advances to procedure block 626.

In procedure block 626, the surgeon attaches the distal cutting block 20 to the base cutting block 12. To do so, the cover 28 is detached from the base cutting block 12, and the distal cutting block 20 aligned with the base cutting block 12. A surgeon may grasp the handles 182 of the lever arms 166 of the distal cutting block and push in the direction indicated by arrow 200 in FIG. 24. When the bias exerted by the springs 190 is overcome, the lever arm 166 is pivoted about the axis 176 from the engaged position to the disengaged position.

The shafts 84 of the base cutting block 12 may then be aligned with the passageways 180 defined in the distal cutting block 20. The distal cutting block 20 may then be advanced over the shafts 84 such that distal cutting block 20 confronts the anterior side surface 82 of the base cutting block 12. The surgeon may then release the handles 182, thereby permitting the lever arms 166 to pivot back to the engaged position. In the engaged position, the catch 94 is received in the recess 92 of the mounting brackets 24 of the base cutting block 12 and engages a posterior surface 90 of the mounting bracket 24 to secure the distal cutting block 20 to the base cutting block 12.

After the distal cutting block 20 is secured to the base cutting block 12, the surgeon may perform the distal resection in procedure block 628. To do so, the surgeon may use the cutting guides 256 defined in the distal cutting block 20, as shown in FIG. 24. For example, the surgeon may select the cutting guide 256 of the distal cutting block 20 corresponding to a desired amount of bone to be removed. The surgeon may perform the distal resection by inserting a bone saw blade 524 into the selected cutting guide 256 of the distal cutting block 20. The surgeon may also utilize fastener guides 262 to attach additional fixation pins to the patient's femur 504.

Figure 25:
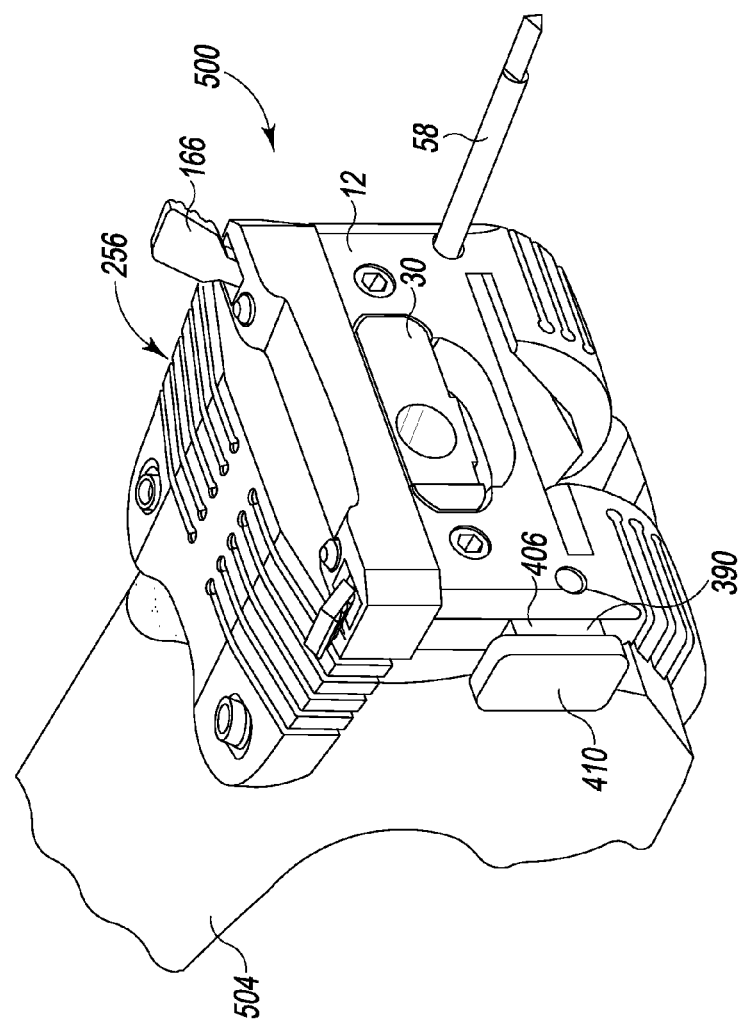

After performing the distal resection, the procedure 600 advances to procedure block 630 in which a distal spacer block 390 is attached to the base cutting block 12. To do so, the surgeon selects the distal spacer block 390 corresponding to the amount of bone removed during the resection. The surgeon may then align the pin 396 of the distal spacer block 390 with the channel 138 defined in the side wall 132. As shown in FIG. 25, the surgeon may then advance the pin 396 into the channel 138 such that the distal spacer block 390 is positioned between the base cutting block 12 and the distal end 502 of the patient's femur 504.

Returning to FIGS. 19A and 19B, when the surgeon determines in procedure block 622 that an augment component is unnecessary, the procedure advances to procedure block 624. In procedure block 624, the anterior cutting block 16 is attached to the base cutting block 12. If a distal resection has been performed, the surgeon first removes the distal cutting block 20 from the base cutting block 12 by operating the lever arm 166 to remove the catches 94 from engagement with the shafts 84 of the base cutting block 12. The surgeon may then attach the anterior cutting block 16 by operating the retention mechanism in a manner similar to that described above. When the anterior cutting block 16 is secured to the base cutting block 12, the procedure 600 advances to procedure block 632.

Figure 26:
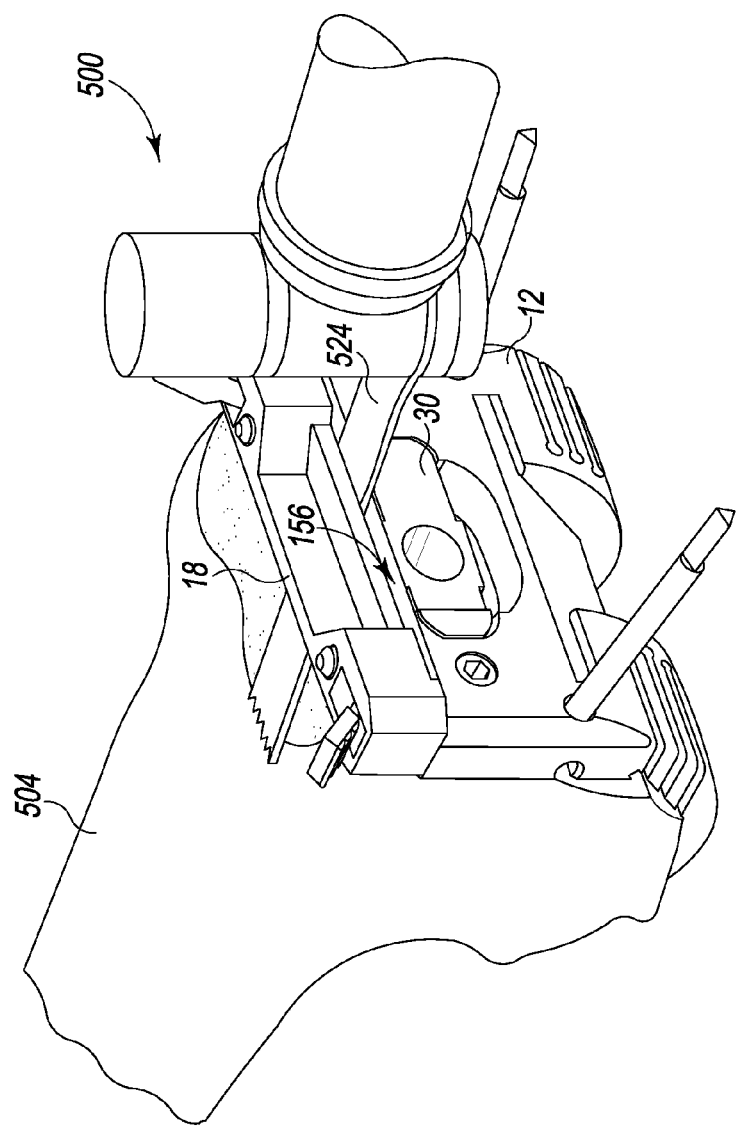

In procedure block 632, the surgeon may use the cutting guide 156 defined in the anterior cutting block 16. As shown in FIG. 26, the surgeon may perform the anterior resection by inserting the bone saw blade 524 into the cutting guide 156 of the anterior cutting block 16. The anterior resection removes an anterior portion of the patient's femur 504 to create a substantially planar anterior surface.

Figure 27:
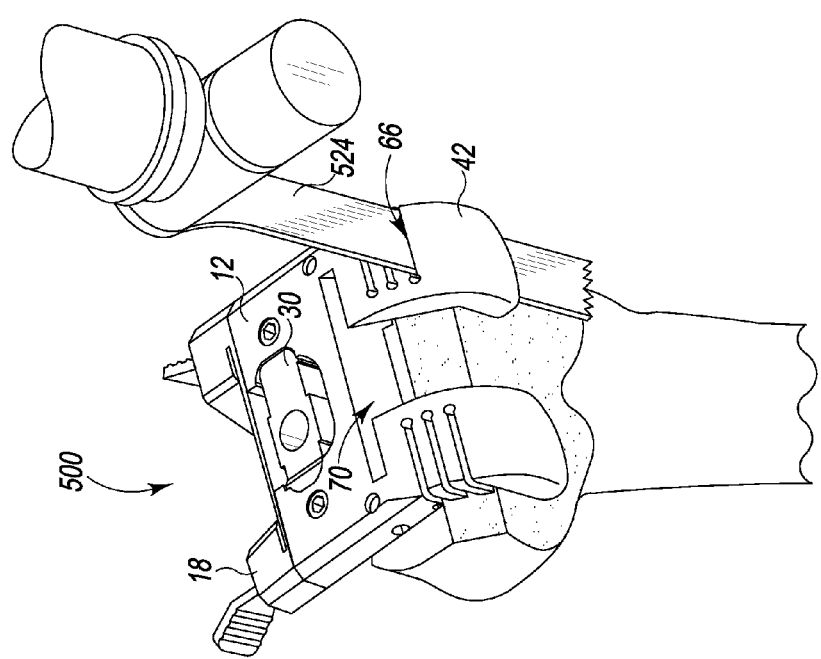

After performing the anterior resection, the surgeon may perform the posterior resection in procedure block 634. To do so, the surgeon may use the posterior cutting guides 68 defined in the base cutting block 12, as shown in FIG. 27. For example, the surgeon may select one or more cutting guides 68 of the base cutting block 12 corresponding to a desired amount of bone to be removed. The surgeon may perform the posterior resection by inserting the bone saw blade 524 into the selected cutting guide 68 and removing posterior portions of the patient's femoral condyles to create a substantially planar surface. The surgeon may also use one or more of the posterior cutting guides 68 to perform a posterior augment resection.

After performing the posterior resection, the procedure 600 advances to procedure block 636 in which the surgeon performs a posterior chamfer resection. In procedure block 636, the surgeon may use the posterior chamfer cutting guide 70 defined in the base cutting block 12. The surgeon may perform the posterior chamfer resection by inserting the bone saw blade 524 into the cutting guide 70 of the base cutting block 12. The posterior chamfer resection removes a posterior chamfer portion of the patient's femur 504 to create a substantially planar anterior surface.

Figure 28:
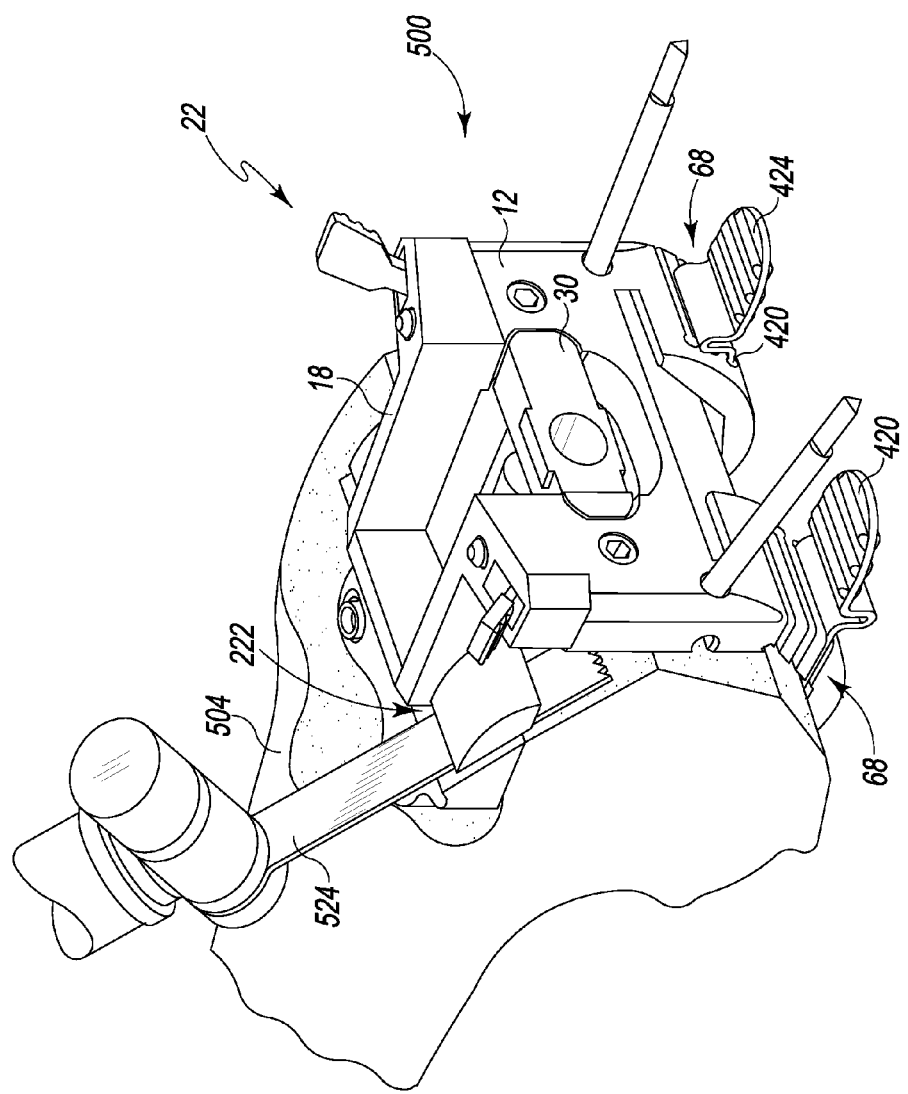

Returning now to FIG. 19B, the procedure 600 advances to procedure block 638 in which the surgeon determines if the instrument construct requires 500 additional stability. If the surgeon decides additional stability is needed, the procedure 600 advances to procedure block 640 in which a posterior shim 420 is inserted into one or more the cutting guides 66 defined in the base cutting block 12. To do so, the surgeon may use the grip 424 inserts the body 422 of a posterior shim 420 into a cutting guide 68, as shown in FIG. 28. When the shim 420 is inserted into the cutting guide 68, the spring 432 engages the base cutting block 12 to retain the posterior shim 420 in the cutting guide 66. The procedure 600 may then proceed to procedure block 642.

In block 642, the surgeon attaches the notch cutting block 18 to the base cutting block 12 after removing the anterior cutting block 16 therefrom. To do so, the surgeon may then attach the notch cutting block 18 by operating the retention mechanism 22 in a manner similar to that described above. When the notch cutting block 18 is secured to the base cutting block 12, the procedure 600 advances to procedure block 644.

In procedure block 644, the surgeon performs an anterior chamfer resection. To do so, the surgeon may use the anterior chamfer cutting guide 222 defined in the notch cutting block 18. The surgeon may perform the anterior chamfer resection by inserting the bone saw blade 524 into the cutting guide 222 as shown in FIG. 28. The anterior chamfer resection removes an anterior chamfer portion of the patient's femur 504 to create a substantially planar anterior surface. As described above, the anterior chamfer cutting guide may be defined in the base cutting block 12 in other embodiments, and in such embodiments the surgeon may use that cutting guide to perform the anterior chamfer resection.

After performing the anterior chamfer resection, the procedure 600 proceeds to procedure block 646 in which the surgeon determines whether a notch cut is required. The surgeon may make that determination based on whether the femoral prosthetic component includes a femoral box. If the surgeon determines that a notch cut is unnecessary, the procedure advances to procedure block 648. If the notch cut is required, the procedure advances to procedure block 650.

Figure 29:
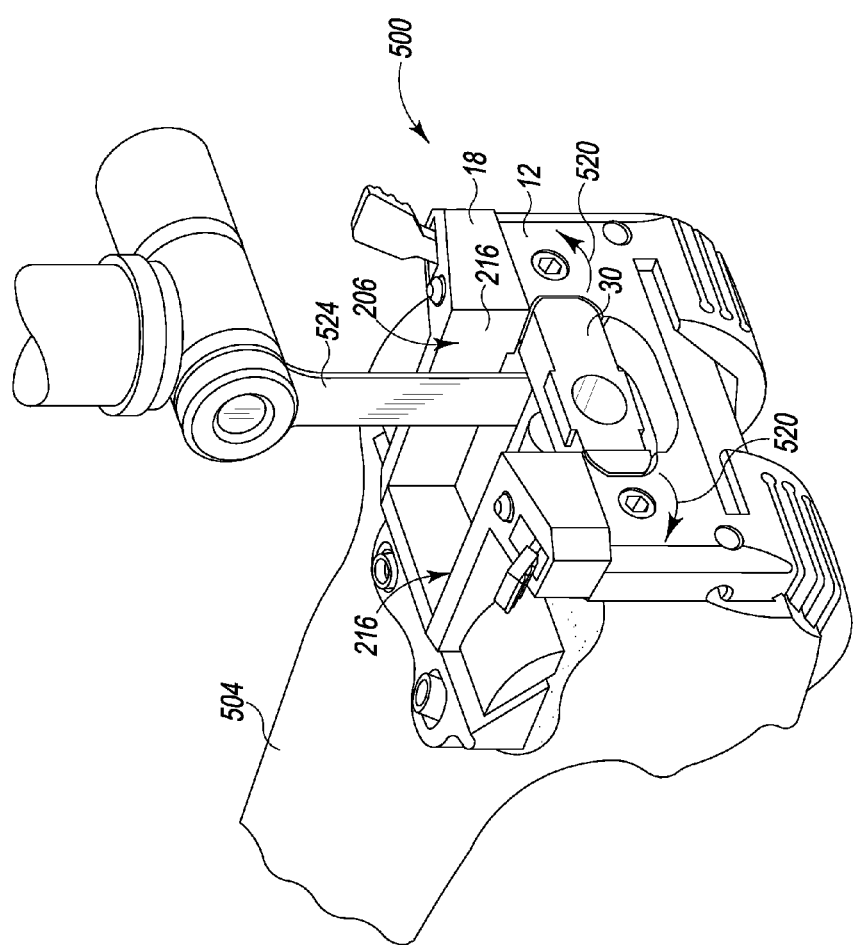
Figure 30:
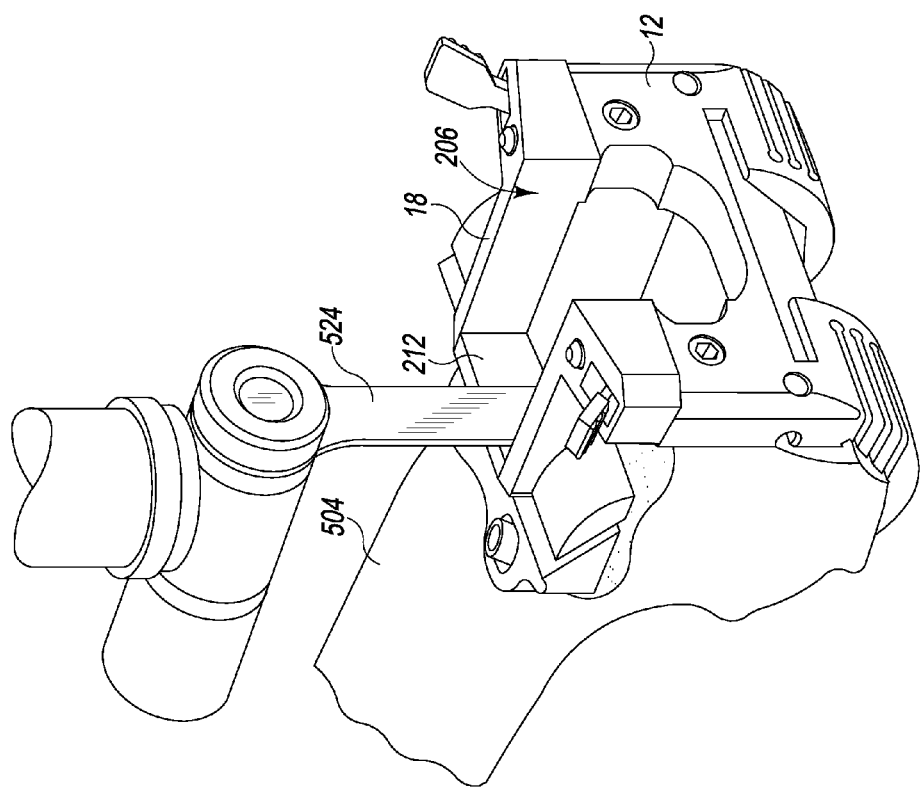

In procedure block 650, the surgeon utilizes the notch cutting guide 206 of the block 18 to remove portions of the patient's femur 504, as shown in FIGS. 29 and 30. To do so, the surgeon may advance the bone saw blade into the cutting guide 206. The surgeon may engage the planar surfaces 216 with the bone saw blade 524 while removing portions of the patient's femur 504.

The surgeon may remove the intramedullary adaptor 30 and the intramedullary orthopaedic surgical instrument 336 before completing the notch cut. To do so, the surgeon may use a driver or other surgical tool to rotate the locking tabs 100, 102 about respective axes 112, 124 as indicated by arrows 530 in FIG. 29. As the locking tabs 100, 102 are rotated, the ears 114, 126 are advanced out of the channels 292, 294 defined in the mounting bracket 280 such that the adaptor 30 is decoupled from the block 12. The adaptor 30 and the intramedullary orthopaedic surgical instrument 336 may then be removed from the patient's femur 504.

As shown in FIG. 30, the surgeon may advance the bone saw blade 524 into the cutting guide 206. The surgeon may engage the planar surface 212 with the bone saw blade 524 to remove a portion of the patient's femur 504, thereby completing the notch cut. After completing the notch cut, the procedure 600 may advance to procedure block 648.

Figure 31:
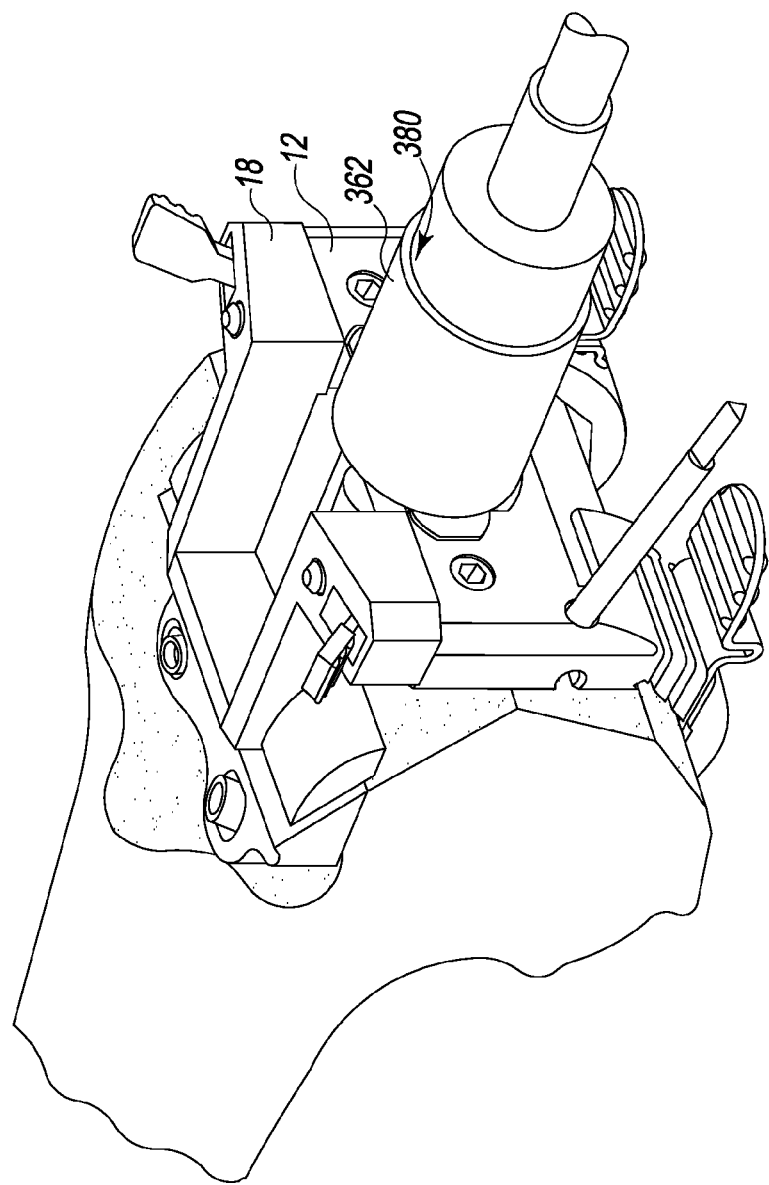

Returning to FIG. 19B, if the surgeon determined in procedure block 646 that a notch cut is unnecessary, the procedure also advance to procedure block 648. In block 648, one of the guide blocks 362, 386 is selected and attached to the base cutting block 12. To do so, the surgeon may select the guide block 362 and position the mounting bracket 364 in the receiving slot 52 of the base cutting block 12, as shown in FIG. 31. A surgeon may use a driver or other surgical tool to rotate the locking tabs 100, 102 about respective axes 112, 124 as indicated. As the locking tabs 100, 102 are rotated, the ears 114, 126 are advanced into the channels 372 defined in the mounting bracket 364, thereby securing the guide block 362 to the block 12.

The procedure 600 may then advance to procedure block 652 in which the surgeon reams the patient's femur 504 to a desired depth. To do so, a reamer 532 may be inserted into the passageway 380 defined in the guide block 362. The reamer 532 may then be engaged with the patient's femur and operated to remove the desired amount of bone.

Figure 32:
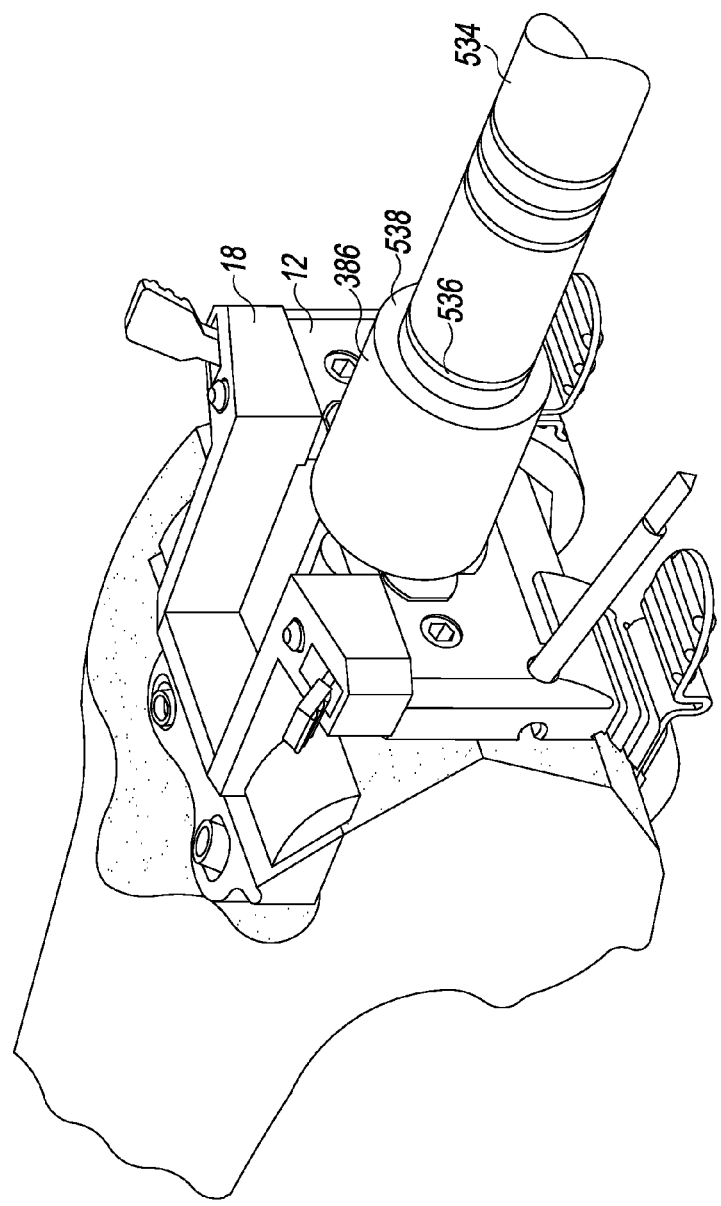

As shown in FIG. 32, the surgeon may select the guide block 386 and attach the block 386 to the base cutting block 12. A reamer 534 may be inserted into the passageway 388 defined in the guide block 386. The reamer 534 may then be engaged with the patient's femur and advanced into the medullary canal 506 until a line 536 corresponding to a desired depth is aligned with the upper surface 538 of the guide block 386.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument assembly comprising:
  a base cutting block comprising:
    a base plate including (i) a proximal surface, (ii) a distal surface positioned opposite the proximal surface, and (iii) a slot extending through the proximal surface and the distal surface, and
    a pair of curved arms extending posteriorly from the base plate, each curved arm including (i) a posterior surface shaped to match a posterior condyle surface of a femoral prosthetic component and (ii) a cutting guide defined in the posterior surface,
  an intramedullary orthopaedic surgical instrument configured to be inserted into a medullary canal of a patient's femur, and
  an adaptor positioned in the slot defined in the base plate, the adaptor including (i) a mounting bracket engaged with the base plate, and (ii) a fastener coupled to the intramedullary orthopaedic surgical instrument.

2. The orthopaedic surgical instrument assembly of claim 1, wherein the base cutting block includes a locking tab pivotally coupled to the base plate, the locking tab being moveable between (i) a first position in which the locking tab is engaged with the mounting bracket to secure the adaptor to the base cutting block, and (ii) a second position in which the locking tab is disengaged from the mounting bracket such that the adaptor is removable from the base cutting block.

3. The orthopaedic surgical instrument assembly of claim 2, wherein the adaptor further includes an adaptor body coupled to the mounting bracket, the adaptor body having a longitudinal axis that forms an oblique angle with an imaginary plane defined by a distal surface of the mounting bracket.

4. The orthopaedic surgical instrument assembly of claim 3, wherein:
  the locking tab of the base cutting block is a first locking tab and the base cutting block includes a second locking tab pivotally coupled to the base plate, and
  the mounting bracket includes (i) a first arm extending outwardly from the adaptor body, the first arm having a channel defined therein that is sized to receive the first locking tab, and (ii) a second arm extending outwardly from the adaptor body opposite the first arm, the second arm having a channel defined therein that is sized to receive the second locking tab.

5. The orthopaedic surgical instrument assembly of claim 3, wherein:
  the adaptor body includes a passageway that extends along the longitudinal axis, and
  the fastener is pivotally coupled to the adaptor body and includes (i) a threaded shaft extending outwardly from the adaptor body and (ii) a head retained in the passageway, the head having a socket shaped to receive a surgical tool to rotate the fastener relative to the adaptor body.

6. The orthopaedic surgical instrument assembly of claim 5, wherein the intramedullary orthopaedic surgical instrument comprises:
  a stem stabilizer having (i) an internally-threaded first end, the internally-threaded first end being engaged with the threaded shaft of the fastener, and (ii) an internally-threaded second end positioned opposite the first end, and
  a stem trial including an externally-threaded end that is engaged with the internally-threaded second end of the stem stabilizer.

7. The orthopaedic surgical instrument assembly of claim 6, wherein the stem stabilizer includes (i) a body having the first end and the second end, and (ii) a pair of fins extending outwardly from the body.

8. The orthopaedic surgical instrument assembly of claim 1, further comprising a guide block configured to be positioned in the slot defined in the base plate in place of the adaptor, wherein the guide block includes a mounting bracket configured to engage with the base cutting block, and a bushing having a cylindrical passageway defined therein sized to receive an orthopaedic surgical instrument.

9. The orthopaedic surgical instrument assembly of claim 1, further comprising a plurality of modular cutting blocks configured to be separately secured to an anterior side of the base plate.

10. An orthopaedic surgical instrument assembly comprising:
  a base cutting block comprising:
    a base plate including (i) a proximal surface, (ii) a distal surface positioned opposite the proximal surface, and (iii) a slot extending through the proximal surface and the distal surface,
    a locking tab having a body positioned between the proximal surface and the distal surface of the base plate and an ear, the body being pivotally coupled to the base plate and moveable between (i) a first position in which the ear of the locking tab is positioned in the slot and (ii) a second position in which the ear is spaced apart from the slot, and
    a pair of curved arms extending posteriorly from the base plate, each curved arm including (i) a posterior surface shaped to match a posterior condyle surface of a femoral prosthetic component and (ii) a cutting guide defined in the posterior surface.

11. The orthopaedic surgical instrument assembly of claim 10, further comprising a first orthopaedic surgical instrument including a mounting bracket, wherein (i) when the body of the locking tab is in the first position, the ear of the locking tab is engaged with the mounting bracket to secure the first orthopaedic surgical instrument to the base plate, and (ii) when the body is in the second position, the ear of the locking tab is disengaged from the mounting bracket such that the first orthopaedic surgical instrument is removable from the base plate.

12. The orthopaedic surgical instrument assembly of claim 11, further comprising a second orthopaedic surgical instrument configured to be secured to a proximal end of the first orthopaedic surgical instrument, the second orthopaedic surgical instrument being an intramedullary orthopaedic surgical instrument.

13. The orthopaedic surgical instrument assembly of claim 10, further comprising a plurality of modular cutting blocks configured to be separately secured to an anterior side of the base plate.

14. The orthopaedic surgical instrument assembly of claim 13, wherein the plurality of modular cutting blocks include an anterior cutting block having an anterior cutting guide defined therein.

15. The orthopaedic surgical instrument assembly of claim 14, wherein:
  at least one of the cutting guides defined in the curved arms of the base cutting block defines an imaginary plane, and
  the plurality of modular cutting blocks include a distal cutting block configured to be secured to the base plate in place of the anterior cutting block, the distal cutting block having a plurality of distal cutting guides, and when the distal cutting block is secured to the base plate, each distal cutting guide extends transverse to the imaginary plane and parallel to the other distal cutting guides.

16. The orthopaedic surgical instrument assembly of claim 14, wherein:

at least one of the cutting guides defined in the curved arms of the base cutting block defines an imaginary plane, and the plurality of modular cutting blocks include a notch cutting block configured to be secured to the base plate in place of the anterior cutting block, the notch cutting block including a first cutting guide having:

a first cutting guide surface that extends transverse to the imaginary plane, and a second cutting guide surface connected to the first cutting guide surface, the second cutting guide surface extending transverse to the imaginary plane and orthogonal to the first cutting guide surface.

17. The orthopaedic surgical instrument assembly of claim 16, wherein the notch cutting block further includes a second cutting guide that extends obliquely relative to the imaginary plane.

18. The orthopaedic surgical instrument assembly of claim 11, further comprising a spacer block configured to be secured to the proximal surface of the base cutting block.

19. The orthopaedic surgical instrument assembly of claim 17, further comprising shim sized to be received in one of the cutting guides defined in the curved arms of the base cutting block.

20. An orthopaedic surgical instrument assembly comprising:

a base block comprising a base plate including (i) a proximal surface, (ii) a distal surface positioned opposite the proximal surface, and (iii) a slot extending through the proximal surface and the distal surface, an intramedullary orthopaedic surgical instrument configured to be inserted into a medullary canal of a patient's femur, an adaptor positioned in the slot defined in the base plate, the adaptor including (i) a mounting bracket engaged with the base plate, (ii) an adaptor body coupled to the mounting bracket and having a longitudinal axis, and (iii) a fastener coupled to the intramedullary orthopaedic surgical instrument and pivotally coupled to the adaptor body, and a plurality of modular cutting blocks configured to be separately secured to an anterior side of the base plate, wherein the adaptor body includes a passageway that extends along the longitudinal axis, and the fastener includes (i) a threaded shaft extending outwardly from the adaptor body and (ii) a head retained in the passageway, the head having a socket shaped to receive a surgical tool to rotate the fastener relative to the adaptor body.

* * * * *